(12) United States Patent
Hansen et al.

(10) Patent No.: US 11,371,166 B2
(45) Date of Patent: Jun. 28, 2022

(54) METHODS FOR DETERMINING LYMPHOCYTE RECEPTOR CHAIN PAIRS

(71) Applicant: THE UNIVERSITY OF BRITISH COLUMBIA, Vancouver (CA)

(72) Inventors: Carl Lars Genghis Hansen, Vancouver (CA); Georgia Elizabeth Mewis, Vancouver (CA); Kevin Albert Heyries, Vancouver (CA); Michael Andrew Vaninsberghe, Vancouver (CA); Daniel Jay Da Costa, Pitt Meadows (CA); Marketa Ricicova, Vancouver (CA)

(73) Assignee: THE UNIVERSITY OF BRITISH COLUMBIA, Vancouver (CA)

( * ) Notice: Subject to any disclaimer, the term of this patent is extended or adjusted under 35 U.S.C. 154(b) by 482 days.

(21) Appl. No.: 16/423,861

(22) Filed: May 28, 2019

(65) Prior Publication Data
US 2019/0300954 A1 Oct. 3, 2019

Related U.S. Application Data

(62) Division of application No. 15/312,909, filed as application No. PCT/CA2015/000328 on May 22, 2015, now Pat. No. 10,400,281.
(Continued)

(51) Int. Cl.
| | |
|---|---|
| *C40B 30/04* | (2006.01) |
| *G16B 30/00* | (2019.01) |
| *G16B 40/00* | (2019.01) |
| *C40B 20/00* | (2006.01) |
| *G01N 33/68* | (2006.01) |
| *C07K 14/725* | (2006.01) |

(Continued)

(52) U.S. Cl.
CPC .......... *C40B 30/04* (2013.01); *C07K 14/7051* (2013.01); *C12Q 1/6876* (2013.01); *C40B 20/00* (2013.01); *G01N 33/68* (2013.01); *G16B 30/00* (2019.02); *G16B 30/10* (2019.02); *G16B 30/20* (2019.02); *G16B 40/00* (2019.02); *C07K 16/00* (2013.01); *C12Q 2600/158* (2013.01)

(58) Field of Classification Search
None
See application file for complete search history.

(56) References Cited

U.S. PATENT DOCUMENTS 8,691,510 B2   4/2014   Faham et al.

FOREIGN PATENT DOCUMENTS

| WO | 2013134162 A2 | 9/2013 |
| WO | 2013134162 A3 | 9/2013 |

(Continued)

OTHER PUBLICATIONS

Dash, P., et al., "Paired analysis of TCRα and TCRβ chains at the single-cell level in mice." The Journal of Clinical Investigation, 2011, 121(1): 288-295.
(Continued)

*Primary Examiner* — Christian C Boesen
(74) *Attorney, Agent, or Firm* — Potomac Law Group, PLLC

(57) ABSTRACT

Provided herein are high-throughput sequencing methods to study the diversity and functionality of lymphocyte receptor chains and pairing of the same. Specifically, the methods provided herein are used to identify with confidence one or more lymphocyte receptor chain pairs in a sample, for example one or more functional chain pairs.

32 Claims, 12 Drawing Sheets

Specification includes a Sequence Listing.

Related U.S. Application Data

(60) Provisional application No. 62/002,152, filed on May 22, 2014.

(51) Int. Cl.
  *G16B 30/20* (2019.01)
  *G16B 30/10* (2019.01)
  *C12Q 1/6876* (2018.01)
  *C07K 16/00* (2006.01)

(56) References Cited

FOREIGN PATENT DOCUMENTS

| WO | 2013188872 A1 | 12/2013 |
|---|---|---|
| WO | 2014145992 A1 | 9/2014 |

OTHER PUBLICATIONS

Embleton. M.J., et al., "In-cell PCR from mRNA: amplifying and linking the rearranged immunoglobulin heavy and light chain V-genes within single cells." Oxford University Press, Nucleic Acid Research, 1992, 20(15): 3831-3837.

Turchaninova. M.A., et al., "Pairing of T-cell receptor chains via emulsion PCR." European Journal of Immunology, 2013, 43: 2507-2515.

Extended European Search Report issued in EP App No. 21151890.7 dated Jul. 21, 2021.

International Preliminary Report on Patentability and Written Opinion issued in International Application No. PCT/CA2015/000328 dated Nov. 22, 2016.

Official Action issue in CA App. No. 2,947,320 dated May 27, 2021.

IDENTIFY PAIRINGS BY PATTERN OF DETECTION ACROSS INDICES

SEQUENCE LISTING

<160> NUMBER OF SEQ ID NOS: 21

<210> SEQ ID NO 1
<211> LENGTH: 126
<212> TYPE: DNA
<213> ORGANISM: Mus musculus

<400> SEQUENCE: 1
tgagtggatt ggaggtattg attcttacaa tggtggtact agctacaacc agaagttcaa     60
gggcaaggcc acattgactg tagacgagtc ctccagcaca gcctacatgg acctccgcag    120
cctgac                                                               126

<210> SEQ ID NO 2
<211> LENGTH: 120
<212> TYPE: DNA
<213> ORGANISM: Mus musculus

<400> SEQUENCE: 2
gattggaggt attgattctt acaatggtgg tactagctac aaccagaagt tcaagggcaa     60
ggccacattg actgtagacg agtcctccag cacagcctac atggacctcc gcagcctgac    120

<210> SEQ ID NO 3
<211> LENGTH: 97
<212> TYPE: DNA
<213> ORGANISM: Mus musculus

<400> SEQUENCE: 3
atggtggtac tagctacaac cagaagttca agggcaaggc acattgact gtagacgagt    60 cctccagcac agcctacatg gacctccgca gcctgac                            97

<210> SEQ ID NO 4
<211> LENGTH: 94
<212> TYPE: DNA
<213> ORGANISM: Mus musculus

<400> SEQUENCE: 4
gtggtactag ctacaaccag aagttcaagg gcaaggccac attgactgta gacgagtcct   60
ccagcacagc ctacatggac ctccgcagcc tgac                               94

<210> SEQ ID NO 5
<211> LENGTH: 91
<212> TYPE: DNA
<213> ORGANISM: Mus musculus

<400> SEQUENCE: 5
gtactagcta caaccagaag ttcaagggca aggccacatt gactgtagac gagtcctcca   60
gcacagccta catggacctc cgcagcctga c                                  91

<210> SEQ ID NO 6
<211> LENGTH: 91
<212> TYPE: DNA
<213> ORGANISM: Mus musculus

<400> SEQUENCE: 6
gtactagcta caaccagaag ttcaagggca aggccacatt gactgtagac gagtcctcca   60
gcacagccta catggacctc cgcagcctga c                                  91

<210> SEQ ID NO 7
<211> LENGTH: 86
<212> TYPE: DNA
<213> ORGANISM: Mus musculus

<400> SEQUENCE: 7
agctacaacc agaagttcaa gggcaaggcc acattgactg tagacgagtc ctccagcaca   60
gcctacatgg acctccgcag cctgac                                        86

<210> SEQ ID NO 8
<211> LENGTH: 60
<212> TYPE: DNA
<213> ORGANISM: Mus musculus

<400> SEQUENCE: 8
ggccacattg actgtagacg agtcctccaa cacagcctac atggacctcc gcagcctgac   60

<210> SEQ ID NO 9
<211> LENGTH: 59
<212> TYPE: DNA
<213> ORGANISM: Mus musculus

<400> SEQUENCE: 9
gccacattga ctgtagacga gtcctccagc acagcctaca tggacctccg cagcctgac    59

<210> SEQ ID NO 10
<211> LENGTH: 55
<212> TYPE: DNA
<213> ORGANISM: Mus musculus

<400> SEQUENCE: 10
cattgactgt agacgagtcc tccagcacag cctacatgga cctccgcagc ctgac    55

<210> SEQ ID NO 11
<211> LENGTH: 99
<212> TYPE: DNA
<213> ORGANISM: Mus musculus

<400> SEQUENCE: 11
tgagtggatt ggaggtattg attcttacaa tggtggtact agctacaacc agaagttcaa    60
gggcaaggcc acattgactg tagacgagtc ctccagcac    99

<210> SEQ ID NO 12
<211> LENGTH: 99
<212> TYPE: DNA
<213> ORGANISM: Mus musculus

<400> SEQUENCE: 12
tgagtggatt ggaggtattg attcttacaa tggtggtact agctacaacc agaagttcaa    60
gggcaaggcc acattgactg tagacgagtc ctccagcac    99

<210> SEQ ID NO 13
<211> LENGTH: 109
<212> TYPE: DNA
<213> ORGANISM: Mus musculus

<400> SEQUENCE: 13
tgagtggatt ggaggtattg attcttacaa tggtggtact agctacaacc agaagttcaa    60
gggcaaggcc acattgactg tagacgagtc ctccagcaca gcctacatg    109

<210> SEQ ID NO 14
<211> LENGTH: 108
<212> TYPE: DNA
<213> ORGANISM: Mus musculus

<400> SEQUENCE: 14
tgagtggatt ggaggtattg attcttacaa tggtggtact agctacaacc agaagttcaa    60
gggcaaggcc acattgactg tagacgagtc ctccagcaca gcctacat    108

<210> SEQ ID NO 15
<211> LENGTH: 97
<212> TYPE: DNA
<213> ORGANISM: Mus musculus

<400> SEQUENCE: 15
tgagtggatt ggaggtattg attcttacaa tggtggtact agctacaacc agaagttcaa    60
gggcaaggcc acattgactg tagacgagtc ctccagc    97

<210> SEQ ID NO 16
<211> LENGTH: 113
<212> TYPE: DNA
<213> ORGANISM: Mus musculus

<400> SEQUENCE: 16

```
tgagtggatt ggaggtattg attcttacaa tggtggtact agctacaacc agaagttcaa    60
gggcaaggcc acattgactg tagacgagtc ctccagcaca gcctacatgg acc          113

<210> SEQ ID NO 17
<211> LENGTH: 109
<212> TYPE: DNA
<213> ORGANISM: Mus musculus

<400> SEQUENCE: 17
tgagtggatt ggaggtattg attcttacaa tggtggtact agctacaacc agaagttcaa    60
gggcaaggcc acattgactg tagacgagtc ctccagcaca gcctacatg              109

<210> SEQ ID NO 18
<211> LENGTH: 108
<212> TYPE: DNA
<213> ORGANISM: Mus musculus

<400> SEQUENCE: 18
tgagtggatt ggaggtattg attcttacaa tggtggtact agctacaacc agaagttcaa    60
gggcaaggcc acattgactg tagacgagtc ctccagcaca gcctacat               108

<210> SEQ ID NO 19
<211> LENGTH: 103
<212> TYPE: DNA
<213> ORGANISM: Mus musculus

<400> SEQUENCE: 19
tgagtggatt ggaggtattg attcttacaa tggtggtact agctacaacc agaagttcaa    60
gggcaaggcc acattgactg tagacgagtc ctccagcaca gcc                    103

<210> SEQ ID NO 20
<211> LENGTH: 109
<212> TYPE: DNA
<213> ORGANISM: Mus musculus

<400> SEQUENCE: 20
tgagtggatt ggaggtattg attcttacaa tggtggtact agctacaacc agaagttcaa    60
gggcaaggcc acattgactg tagacgagtc ctccagcaca gcctacatg              109

<210> SEQ ID NO 21
<211> LENGTH: 15
<212> TYPE: DNA
<213> ORGANISM: Mus musculus

<400> SEQUENCE: 21
tgagtggatt ggagg                                                    15
```

METHODS FOR DETERMINING LYMPHOCYTE RECEPTOR CHAIN PAIRS

CROSS REFERENCE TO RELATED APPLICATIONS

This application is a divisional of U.S. application Ser. No. 15/312,909, filed Nov. 21, 2016, which is a U.S. National Stage Application of International Patent Application No. PCT/CA2015/000328, filed May 22, 2015, which claims the benefit of U.S. Provisional Application Ser. No. 62/002,152, filed May 22, 2014, the disclosures of which are hereby incorporated by reference in their entireties.

The Sequence Listing for this application is labeled "SeqList-15Feb19-ST25.txt", which was created on Feb. 15, 2019 and is 5 KB. The entire content is incorporated herein by reference in its entirety.

BACKGROUND OF THE INVENTION

Antibodies are effector proteins in the adaptive immune system. Each antibody is made up of a heterodimeric complex consisting of two linked heavy chains, and each individual heavy chain is linked to an identical light chain. At the end of the heavy and light chains is a variable region that, when in complex, combines to form the "paratope" of the antibody. The paratope is the section of the antibody that gives specificity to binding, allowing each different antibody to recognize a unique "epitope" which is a structure presented by an antigen. The adaptive immune systems of jawed vertebrates are capable of generating a large diversity of possible antibodies—in theory being ~$10^{14}$ for humans.

The diversity of antibodies is created by two processes: 1) the process of gene recombination and 2) the process of somatic hypermutation and affinity maturation. Gene recombination occurs during B cell development and results in a seemingly random combination of several regions of the genome (e.g., VDJ recombination in heavy chains) to create a functional antibody sequence. In addition to the combinatorial diversity of gene usage, this process also results in non-templated base additions or deletions at the junctions. The same process happens in the light chains to create a unique light chain. In some species, including rabbits and chickens, antibody diversity is also generated through a process of gene conversion.

Within each mature B cell, a unique heavy and light chain come together to create a unique antibody sequence that is displayed as a receptor (BCR) on the surface of the B cell. After challenge by a foreign antigen, if a BCR binds to the antigen (and also receives appropriate signals from T cells) the B cell divides and expands. During this division somatic mutation occurs within the genes encoding antibody variable regions. If the mutation improves binding to the antigen, the B cell continues to divide and obtains a selective advantage, whereas if the mutation destroys binding, the cell ultimately dies. As a result, each mature B cell that recognizes a given antigen gives rise to a diversity of different, but closely related, antibodies that have optimized binding properties.

T cell receptors (TCRs), displayed on mature T cells, are created by a similar process of gene recombination with the following differences: (i) TCRs are formed by a simple dimer complex (for example consisting of an alpha and a beta chain), (ii) TCRs do not undergo somatic hypermutation or affinity maturation, (iii) TCRs do not recognize native antigens but rather MHC-peptide complexes displayed by cells, and (iv) TCR formation is subject to stricter regulation to ensure recognition of MHC and to avoid auto-reactivity (the latter also happens with BCRs but to a lesser extent).

SUMMARY OF THE INVENTION

In one aspect of the invention, a method is provided for identifying a plurality of lymphocyte receptor chain pairs in a sample comprising a plurality of lymphocytes or progeny thereof. In one embodiment of this method, the sample is optionally subjected to conditions suitable for expansion of one or more of the plurality of lymphocytes to optionally form an expanded sample. The sample or expanded sample is partitioned into a plurality of individual vessels to provide a plurality of sample subpopulations. One or more sample subpopulations are optionally subjected to conditions suitable for expansion of one or more of the lymphocytes in the one or more of the sample subpopulations; to optionally form one or more expanded sample subpopulations. Nucleic acid (polynucleotides) clonotypes from each sample subpopulation encoding the lymphocyte receptor chains are sequenced from each sample subpopulation to determine the identity of the lymphocyte receptor chains in each subpopulation. Nucleic acid clonotypes in one embodiment are genomic DNA fragments while in other embodiments, are complementary DNA (cDNA fragments), generated by a first strand cDNA synthesis reaction of the lymphocyte receptor chain mRNA in the sample. The observed distribution of each of the lymphocyte receptor chains across the subpopulations is then determined. From the observed distribution, statistical probabilities that the lymphocyte receptor chain occurrences are independent from one another are calculated. The plurality of lymphocyte receptor chain pairs present in the sample is then determined based on the statistical probabilities.

In a further embodiment, the sample is subjected to conditions suitable for expansion of one or more of the lymphocytes to form an expanded sample and/or subjecting one or more of the sample subpopulations to conditions suitable for expansion of one or more of the lymphocytes in the one or more of the sample subpopulations; to form one or more expanded sample subpopulations.

In one embodiment, one or more of the sample subpopulations is subjected to conditions suitable for expansion of one or more of the lymphocytes or progeny thereof in the one or more of the sample subpopulations; to form one or more expanded sample subpopulations. In a further embodiment, the one or more expanded sample subpopulations is purified and/or enriched for, to provide one or more expanded enriched subpopulations. In even a further embodiment, sequencing the nucleic acid clonotypes comprises sequencing the nucleic acid clonotypes in each expanded enriched subpopulation.

In another aspect of the invention, a method for identifying a functional lymphocyte receptor chain pair in a sample comprising a plurality of lymphocytes is provided. In one embodiment of this method, a sample is optionally subjected to conditions suitable for expansion of one or more of the plurality of lymphocytes to form an optionally expanded sample. The sample or expanded sample is partitioned into a first plurality of individual vessels to provide a plurality of sample sub-populations. A functional assay is performed on one or more of the plurality of subpopulations, or one or more subsamples thereof, wherein the functional assay measures a property of a lymphocyte receptor chain pair. The functional assay can be carried out in the same vessel in which the respective subpopulation was partitioned or a different vessel (e.g., microfluidic chamber, microtiter well, microfuge tube, array plate, cell culture plate, etc.). Based on the results of the functional assay, one or more functional subpopulations are identified. The one or more functional subpopulations are optionally partitioned into a second plurality of individual vessels to optionally provide a plurality of sub-subpopulations. Optionally, the one or more functional subpopulations or one or more of the sub-subpopulations is subjected to conditions suitable for expansion of one or more of the lymphocytes in the one or more functional subpopulations or one or more sub-subpopulations to optionally form an expanded functional subpopulation or expanded sub-subpopulation. Nucleic acid clonotypes encoding the lymphocyte receptor chains from each sample sub-subpopulation are sequenced to determine the identity of the lymphocyte receptor chains in each sub-subpopulation. The nucleic acid clonotypes in one embodiment are genomic DNA fragments while in another embodiment, are complementary DNA (cDNA fragments), generated by a first strand cDNA synthesis reaction of the lymphocyte receptor chain mRNA in the sample. In another embodiment, mRNA fragments are sequenced directly. The observed distribution of each of the lymphocyte receptor chains across the functional subpopulations or sub-subpopulations is then determined. From the observed distribution, statistical probabilities that the lymphocyte receptor chain occurrences are independent from one another are calculated. The functional lymphocyte receptor chain pair is identified based on the calculated statistical probabilities.

In one embodiment of the method, the sample is subjected to conditions suitable for expansion of one or more of the plurality of lymphocytes to form an expanded sample and/or one or more of the sub-subpopulations is subjected to conditions suitable for expansion of one or more of the lymphocytes in the one or more sub-subpopulations to form an expanded sub-subpopulation.

In one embodiment, one or more of the functional subpopulations or sub-subpopulations is subjected to conditions suitable for expansion of one or more of the lymphocytes in the one or more functional subpopulations or sub-subpopulations to form an expanded functional subpopulation or expanded sub-subpopulation. In a further embodiment, the one or more expanded functional subpopulation or one or more expanded sub-subpopulation are purified and/or enriched for, to provide an expanded enriched functional subpopulation or expanded enriched sub-subpopulation. In even a further embodiment, sequencing the nucleic acid clonotypes comprises sequencing the nucleic acid clonotypes in each expanded enriched functional subpopulation or expanded enriched sub-subpopulation.

In one embodiment, a unique DNA barcode sequence is attached to the nucleic acid (genomic DNA, mRNA or cDNA) in each sub-subpopulation prior to sequencing, wherein the unique DNA barcode sequence identifies the sub-subpopulation from which the nucleic acid fragments originated.

In one embodiment, one or more of the optional steps provided herein is carried out.

In one embodiment, sequencing nucleic acid clonotypes comprises direct sequencing of mRNA and/or sequencing of cDNA.

Another aspect of the methods provided herein, a barcode-free approach is used to identify nucleic acid clonotypes from individual containers, subpopulations or sub-populations. For example, in one embodiment, fusion pairs of lymphocyte receptor chains are generated for each receptor chain population in the individual vessels or containers.

In a further embodiment, the fusion pairs of lymphocyte receptor chains comprise TCR α-α, TCR β-β, TCR γ-γ, TCR δ-δ, BCR/Ab heavy-heavy, BCR/Ab light-light), TCR α-β, TCR γ-δ, TCR γ-α, TCR γ-β, TCR δ-α, TCR δ-β, BCR/Ab heavy-light, TCR α-BCR/Ab heavy pairs, or a combination thereof.

Yet another aspect of the invention provided herein relates to a composition comprising one or more of the functional lymphocyte receptor chain pairs identified one or more of the methods set forth herein.

As can be seen, all of the chains were correctly co-localized for varying starting number of containers per chain.

Figure 18:
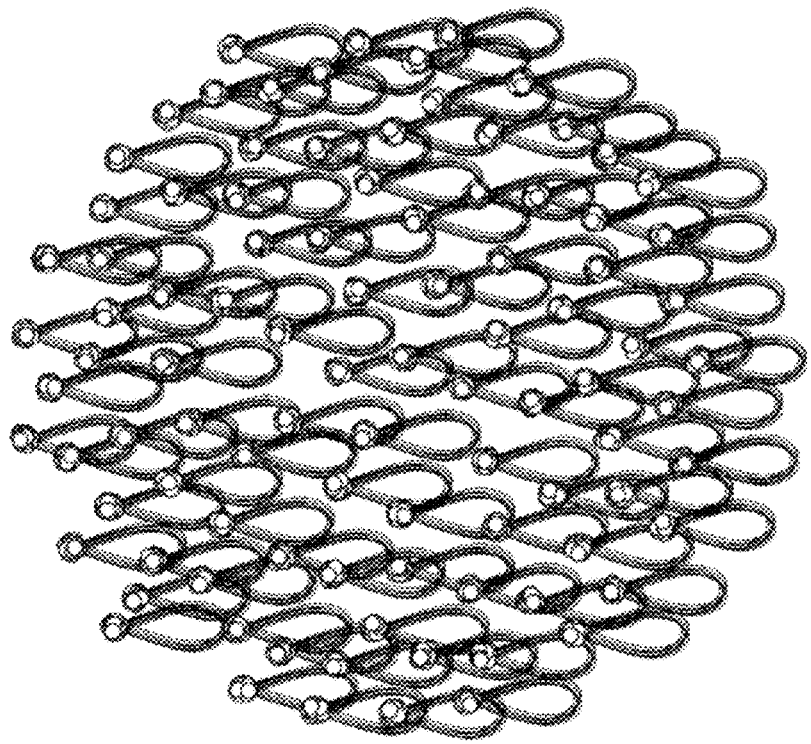

FIG. 18 is a network diagram of the minimally-connected vertices identified from a partitioning and fusion simulation experiment with 1000 cells partitioned into each of 96 containers and a read-depth of 83× per cell. Colours indicate the 96 different communities correctly identified using Walktrap community detection. These minimally-connected communities were used to correctly classify the highly-connected vertices.

Figure 19:
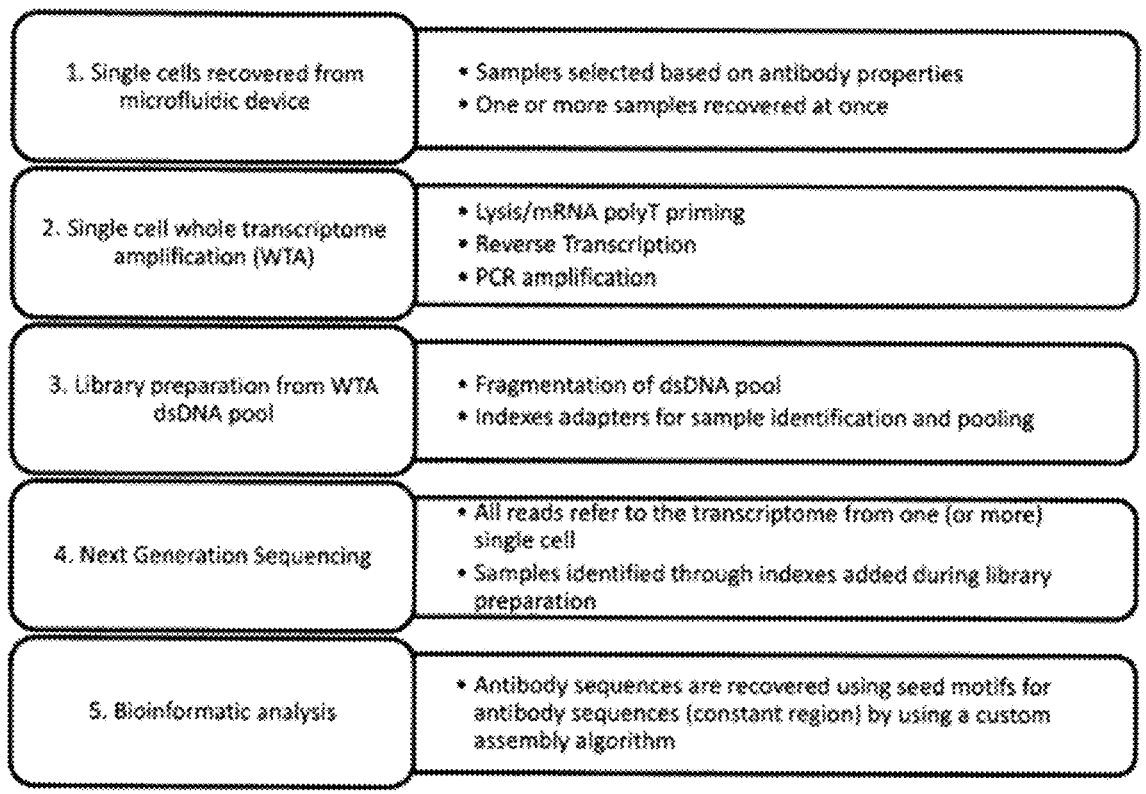

FIG. 19 is an embodiment of the general workflow for the identification of lymphocyte receptor chain pair sequences from whole transcriptome amplified products using next generation sequencing without gene specific primers.

Figure 20:
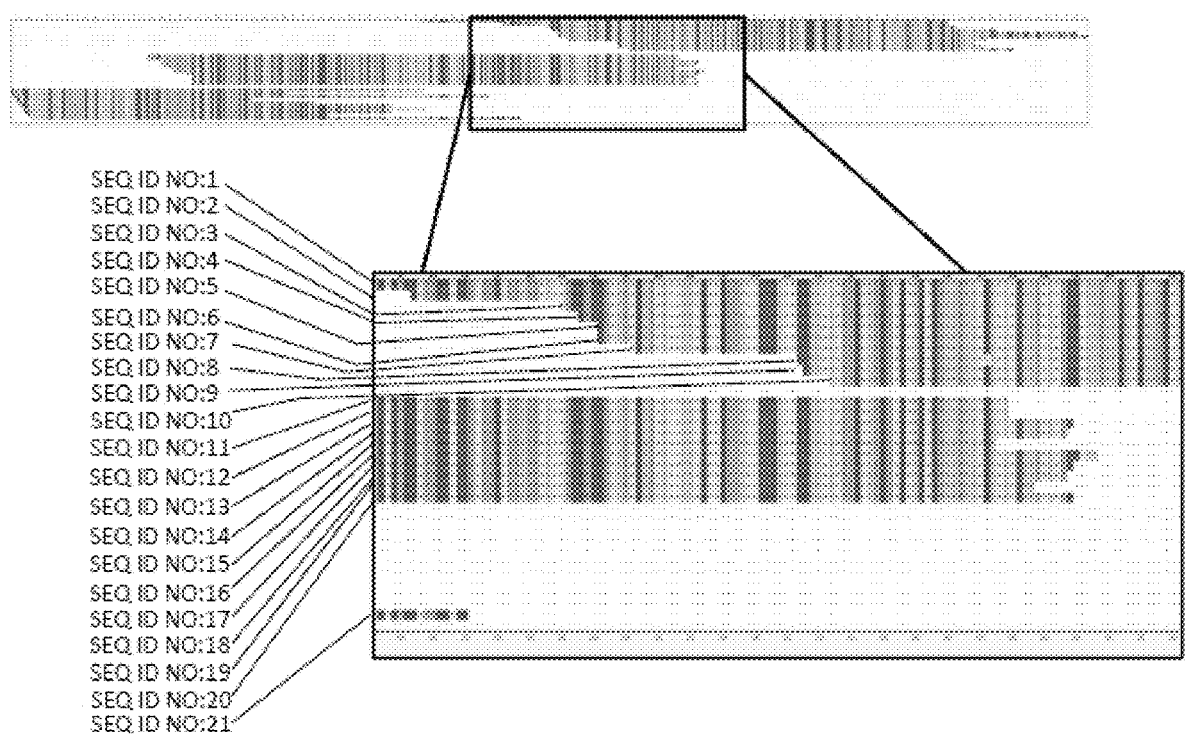

FIG. 20 is a graphical example of the assembly process using reads (SEQ ID NOs: 1-21) obtained from a next generation sequencing run.

DETAILED DESCRIPTION OF THE INVENTION

The analysis of immunoglobin genes and TCR genes using high-throughput sequencing (Ig-Seq or TCR-Seq as used herein) has emerged as a powerful tool for studying the dynamics and evolution of immune responses. In addition to studying the fundamental biology of immune responses, these high throughput sequencing technologies offer the possibility of mining complete immune repertoires to identify new antibodies with desired properties or to evaluate the nature of immune responses to vaccination or immunization. However, although Ig-Seq provides comprehensive lists of heavy and light chain variable regions that exist within an antibody repertoire, it does not provide a means to interpret the functional significance of these sequences. Specifically, Ig-Seq does not provide information on the correct chain-pairing of heavy and light sequences, which is needed to identify and recover functional antibodies. Nor does it provide information regarding the functional or binding characteristics of the antibody. In addition, errors introduced in sequencing and PCR, as well as amplification bias, make it difficult to assess the true diversity of antibody sequences, TCRs, or their relative frequency on a cell-by-cell basis simply by performing high throughput sequencing of the heavy and light chains of antibodies, or the alpha and beta chains of TCRs.

There is a high interest in using new high-throughput sequencing technologies to study the diversity of antibody, B-cell receptor and T-cell receptor sequences. As described herein, a "lymphocyte receptor chain pair" is meant to encompass each of the aforementioned molecules, specifically, heavy and light chain pairs of antibodies, B-cell receptor heavy and light chain pairs and T-cell receptor chain pairs. In one embodiment, the T-cell receptor chain pair is an alpha and beta chain pair, a delta and gamma chain pair, or a combination thereof.

Applications of this "immune profiling" include monitoring patients for disease, searching for and identifying new antibodies (e.g., therapeutic antibodies), and understanding the dynamics and health of immune systems. A major challenge in existing approaches is that when sequencing is performed it is typically done on huge numbers of cells to profile the entire immune repertoire. This involves lysing many cells and mixing their nucleic acid prior to sequencing. As a result, information regarding the correct pairing of lymphocyte receptor chains is lost. This information is critical to being able to reconstitute the immune system. The present invention addresses this problem by providing methodology for identifying correct pairing of lymphocyte receptor chains.

As used herein, a "lymphocyte clone" or "clone" is a lymphocyte cell or progenitor thereof (i.e., an antibody secreting cell") that expresses a unique lymphocyte receptor chain pair, as compared to other "lymphocyte clones" in the sample. A clone is expresses a recombined nucleotide sequence of a lymphocyte receptor. A lymphocyte clone in one embodiment is a T-cell or B-cell or an ASC. A "clonotype" is the nucleotide sequence that encodes an entire rearranged lymphocyte receptor chain, or a portion thereof. For example, a clonotype in one embodiment, encodes all or a portion of a VDJ rearrangement of IgH, a DJ rearrangement of IgH, a VJ rearrangement of IgK, a VJ rearrangement of IgL, a VDJ rearrangement of TCR β, a DJ rearrangement of TCR β, a VJ rearrangement of TCR a, a VJ rearrangement of TCR γ, a VDJ rearrangement of TCR δ, a VD rearrangement of TCR δ, a Kde-V rearrangement, or the like. In one embodiment, a clonotype sequence is sufficient to represent or reflect the immune molecule that the clonotype is derived from. Accordingly, clonotypes in one embodiment, vary in length. In one embodiment, a clonotype has a nucleotide length in the range of from about 25 to about 400 nucleotides. In a further embodiment, a clonotype has a length of from about 25 to 300 nucleotides, or from about 25 to about 250 nucleotides, or from about 25 to about 200 nucleotides. A clonotype can refer to both RNA and DNA sequences. In the methods provided herein, nucleic acid sequencing of a lymphocyte receptor chain comprises sequencing a clonotype corresponding to said chain.

A lymphocyte clone can be present multiple times in any sample. The methods as described herein can be used to identify with confidence the repertoire of lymphocyte receptor chain pairs, or a subset thereof (e.g., a functional subset) in a sample, for example a sample derived from a human. Moreover, the methods presented herein are amenable for the identification of both T-cell receptor (TCR) chain pairs, and B-cell receptor (BCR) chain pairs (including antibody chain pairs, i.e., heavy and light chain pairs) and B-cell progeny (antibody secreting cells, or "ASCs"). In other embodiments, the methods provided herein are used to identify one or more rare lymphocyte receptor chain pairs in a sample, where the lymphocyte receptor chain pair is expressed by a lymphocyte clone present at a frequency of about 1 cell to about 50 cells in the sample, or expressed by a lymphocyte clone present at about a frequency of 1 percent or less, of the total lymphocyte clone population in the sample.

For example, in one embodiment of the invention, a method for determining a lymphocyte receptor chain pair, e.g., a receptor chain pair from a T-cell, B-cell or ASC expressed by a "low frequency" clone is provided. For example, in one embodiment, the present invention provides a method for determining a lymphocyte receptor chain pair (e.g., α and β T-cell receptor chain pair; γ and δ T-cell receptor chain pair; heavy and light antibody chain pair, or a combination thereof) of a lymphocyte clone that is present in the sample at a frequency of about 1 cell, about 2 cells, about 3 cells, about 4 cells, about 5 cells, about 6 cells, about 7 cells, about 8 cells, about 9 cells, or about 10 cells. In another embodiment, the clone is present in the sample at a frequency of from about 1 cell to about 20 cells, or from about 1 cell to about 15 cells, or from about 1 cell to about 10 cells or from about 1 cell to about 5 cells. In yet another embodiment, the clone is present in the sample at a frequency of from about 1 cell to about 50 cells, or from about 5 cells to about 50 cells, or from about 5 cells to about 25 cells, or from about 2 cells to about 10 cells. In even another embodiment, the clone is present in the sample at a frequency of 1 percent or less, 0.5 percent or less, 0.1 percent or less, or from about 0.01 percent to about 2 percent, or from about 0.1 percent to about 2 percent, or from about 0.01 percent to about 1 percent, or from about 0.1 percent to about 1 percent, or about 1 percent to about 2 percent, of the total lymphocyte clone population in the sample The methods provided herein can be used in an array of applications including monitoring patients for disease, searching for new antibodies, and understanding the dynamics and health of immune systems. A major challenge in current approaches is that when sequencing is performed it is typically done on huge numbers of cells to profile the entire immune repertoire. This involves lysing many cells and mixing their RNA prior to sequencing. As a result, information regarding the correct pairing of lymphocyte receptor chain pairs, including rare lymphocyte receptor chain pairs is lost. This pairing information is critical to being able to decipher the immune repertoire of a subject. The present invention addresses this and other needs.

Figure 1:
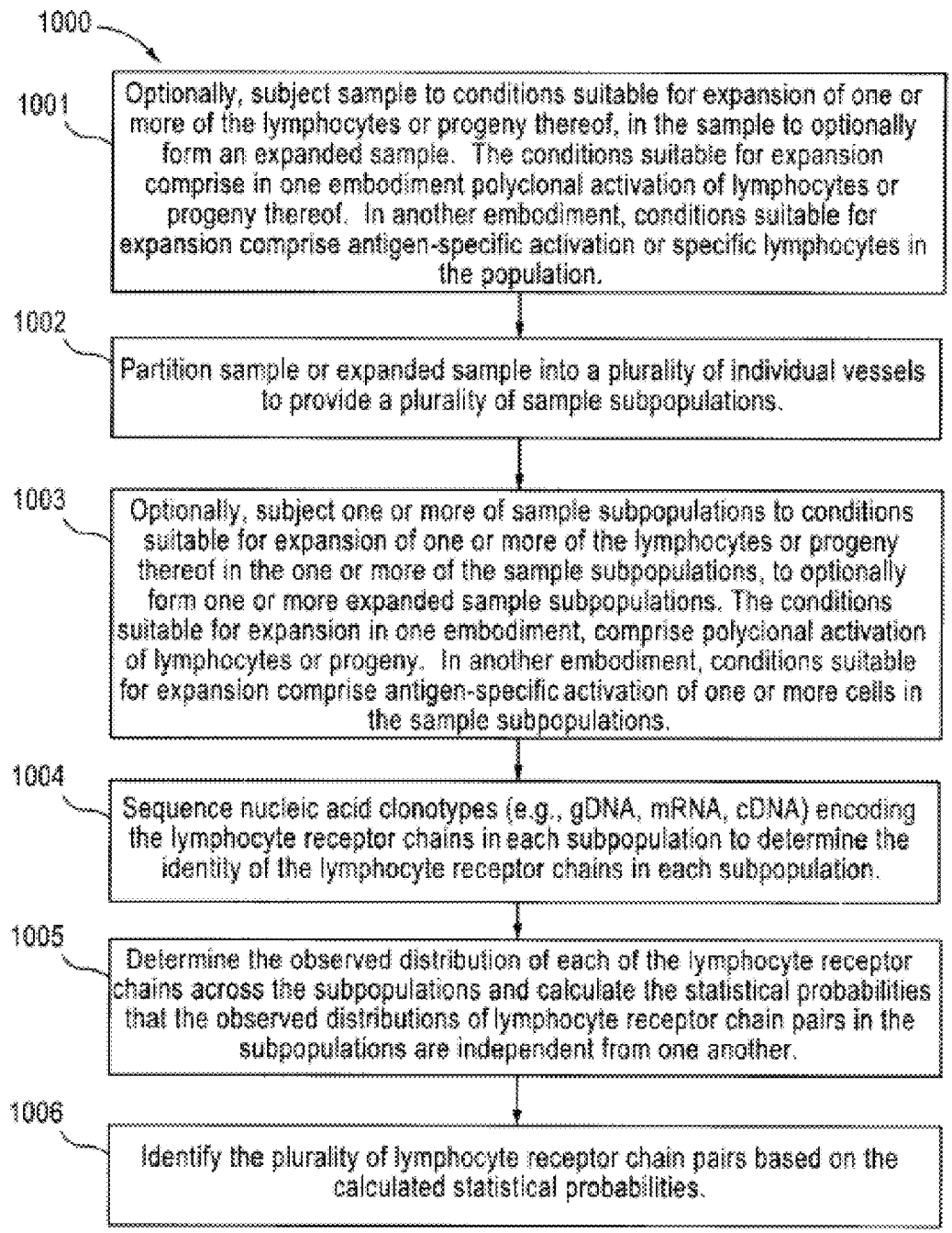
FIG. 1 is a flow chart setting forth one aspect of the invention.

FIG. 1 is a flow chart showing one aspect (1000) of the present invention, i.e., a method for identifying a plurality of lymphocyte receptor chain pairs in a sample comprising a plurality of lymphocytes. According to this aspect, the sample is optionally subjected to conditions suitable for expansion of one or more of the plurality of lymphocytes to optionally form an expanded sample (1001). The sample or expanded sample is partitioned into a plurality of individual vessels to provide a plurality of sample subpopulations (1002). One or more sample subpopulations are optionally subjected to conditions suitable for expansion of one or more of the lymphocytes in the one or more of the sample subpopulations; to optionally form one or more expanded sample subpopulations (1003). Nucleic acid encoding the lymphocyte receptor chains (i.e., nucleic acid clonotypes) are sequenced from each sample subpopulation to determine the identity of the lymphocyte receptor chains in each subpopulation (1004). The nucleic acid in one embodiment are genomic DNA fragments while in other embodiments, are mRNA sequences, or complementary DNA (cDNA fragments), generated by a first strand cDNA synthesis reaction of the lymphocyte receptor chain mRNA in the sample. The observed distribution of each of the lymphocyte receptor chains across the subpopulations is then determined (1005). From the observed distribution, statistical probabilities that the lymphocyte receptor chain occurrences are independent from one another are calculated. The plurality of lymphocyte receptor chain pairs present in the sample is then determined based on the statistical probabilities (1006).

In one embodiment of the method set forth in FIG. 1, the sample is subjected to conditions suitable for expansion of one or more of the lymphocytes to form an expanded sample. In another embodiment, one or more of the sample subpopulations are subjected to conditions suitable for expansion of one or more of the lymphocytes in the one or more of the sample subpopulations; to form one or more expanded sample subpopulations.

Figure 2:
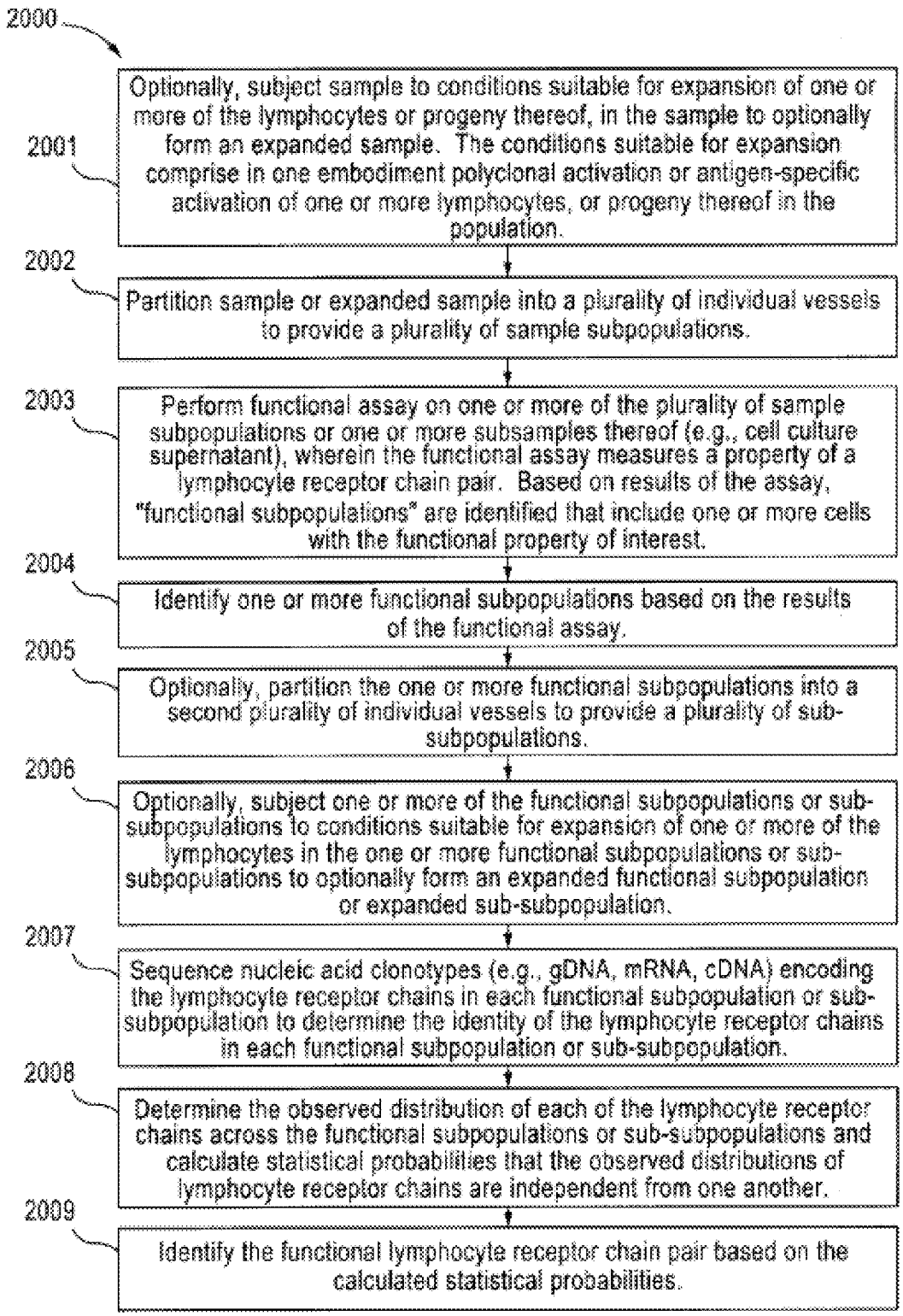
FIG. 2 is a flow chart setting forth a second aspect of the invention.

FIG. 2 is a flow chart showing a second aspect of the present invention (2000), i.e., a method for identifying a functional lymphocyte receptor chain pair in a sample comprising a plurality of lymphocytes. In this aspect, a sample is optionally subjected to conditions suitable for expansion of one or more of the plurality of lymphocytes to form an optionally expanded sample (2001). The sample or expanded sample is partitioned into a first plurality of individual vessels to provide a plurality of sample subpopulations (2002). A functional assay is performed on one or more of the plurality of subpopulations, or one or more subsamples thereof, wherein the functional assay measures a property of a lymphocyte receptor chain pair (2003). The functional assay can be carried out in the same vessel in which the respective subpopulation was partitioned, or a different vessel (e.g., microfluidic chamber, microtiter well, microfuge tube, array plate, etc.). Based on the results of the functional assay, one or more functional subpopulations are identified (2004). Optionally, the one or more functional subpopulations are partitioned into a second plurality of individual vessels to provide a plurality of sub-subpopulations (2005). Optionally, one or more of the functional subpopulations or sub-subpopulations is subjected to conditions suitable for expansion of one or more of the lymphocytes in the one or more functional subpopulations or sub-subpopulations to optionally form an expanded functional subpopulation or sub-subpopulation (2006). Nucleic acid clonotypes encoding the lymphocyte receptor chains from each sample sub-subpopulation are sequenced to determine the identity of the lymphocyte receptor chains in each sub-subpopulation (2007). The nucleic acid in one embodiment is genomic DNA fragments while in another embodiment, are mRNA or complementary DNA (cDNA fragments), generated by a first strand cDNA synthesis reaction of the lymphocyte receptor chain mRNA in the sample. The observed distribution of each of the lymphocyte receptor chains across the sub-subpopulations is then determined and from the observed distribution, statistical probabilities that the lymphocyte receptor chain occurrences are independent from one another are calculated (2008). The functional lymphocyte receptor chain pair is identified based on the calculated statistical probabilities (2009).

In one embodiment of the method set forth in FIG. 2, the sample is subjected to conditions suitable for expansion of one or more of the plurality of lymphocytes to form an expanded sample. In another embodiment, the functional subpopulations are partitioned into a second plurality of individual vessels to provide a plurality of sub-subpopulations. In a further embodiment, one or more of the plurality of the sub-subpopulations is subjected to conditions suitable for expansion of one or more of the lymphocytes in the one or more sub-subpopulations to form an expanded sub-subpopulation Other embodiments of the methods set forth in FIGS. 1 and 2 are discussed throughout.

The sample subjected to one of the methods described herein comprises a plurality of lymphocytes, wherein each lymphocyte expresses a lymphocyte receptor chain pair. In the case of a T-lymphocyte (also referred to as "T-cell"), the lymphocyte receptor chain pair is a T-cell receptor (TCR) chain pair, while in the case of a B-lymphocyte (also referred to as "B-cell") or one of its progeny, the lymphocyte receptor chain pair is an immunoglobulin (Ig) chain pair (i.e., heavy chain and light chain pair). A plurality of lymphocytes can comprise any combination of one or more T-cells, one or more B-cells, and/or one or more antibody secreting cells ("ASCs").

As will be understood by one of ordinary skill in the art, a lymphocyte clone can be present multiple times in the sample, e.g., by dividing once it is activated. As an example, each T-lymphocyte (T-cell) clone expresses a unique T-cell receptor chain pair. T-cells include helper T cells ("effector T cells" or "Th cells"), cytotoxic T cells ("Tc," "CTL" or "killer T cell"), memory T cells, and regulatory T cells. Other examples of T cells include, for example, CD8+ T cells, CD4+ T cells, and recombinant cells engineered to express a T cell receptor. In one embodiment, the present invention provides methods for determining the alpha ($\alpha$) and beta ($\beta$) T-cell receptor chain pair (i.e., the $\alpha\beta$ T-cell receptor chain pair or heterodimer). T-cells that express $\alpha$ and $\beta$ receptor pairs are referred to herein as $\alpha$:$\beta$ T-cells or $\alpha\beta$ T-cells. In another embodiment, the present invention provides methods for determining one or more gamma ($\gamma$) and delta ($\delta$) T-cell receptor chain pairs (i.e., the $\gamma\delta$ T-cell receptor chain pair or heterodimer) from a sample comprising a plurality of lymphocytes or progenitors thereof. T-cells that express $\gamma$ and $\delta$ receptor pairs are referred to herein as $\gamma$:$\delta$ T-cells or $\gamma\delta$ T-cells.

Each TCR chain (i.e., $\alpha$, $\beta$, $\gamma$ and $\delta$ polypeptide) contains variable complementarity determining regions (CDRs), as well as framework regions (FRs) and a constant region. The sequence diversity of $\alpha\beta$ T cells is largely determined by the amino acid sequence of the third complementarity-determining region (CDR3) loops of the a and $\beta$ chain variable domains, which diversity is a result of recombination between variable (V), diversity (Dp), and joining (Jp) gene segments in the $\beta$ chain locus, and between analogous V$\alpha$ and J$\alpha$ gene segments in the $\alpha$ chain locus, respectively. The existence of multiple such gene segments in the TCR $\alpha$ and $\beta$ chain loci allows for a large number of distinct CDR3 sequences to be encoded.

Immunoglobulins (Igs) are expressed by B-cells, and are a type of lymphocyte receptor, as the term is used herein. Igs in a membrane bound state are referred to herein as B cell receptors (BCR), and when secreted by a cell, are referred to as antibodies. Each Ig is a protein consisting of four polypeptide chains, two identical heavy chains (H chains) from the immunoglobulin heavy locus (IGH) and two identical light chains (L chains) from either the IGκ (kappa) or the IGλ (lambda) locus, forming an $H_2L_2$ structure. In embodiments described herein, methods are provided for determining a heavy chain—light chain pair from a sample comprising a plurality of lymphocytes or progeny thereof, e.g., B-cells or engineered ASCs.

Figure 3:
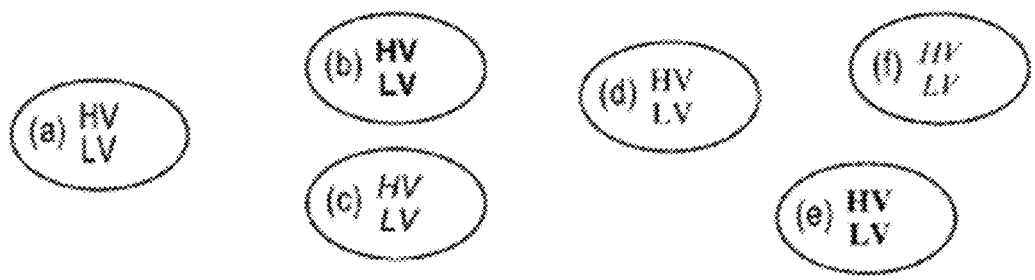
FIG. 3 is a cartoon depiction of a population of B cells, each encoding a unique antibody comprising a unique heavy and light chain combination. Each unique cell is labeled "(a)", "(b)", "(c)", "(d)", "(e)" and "(f)".
Figure 4:
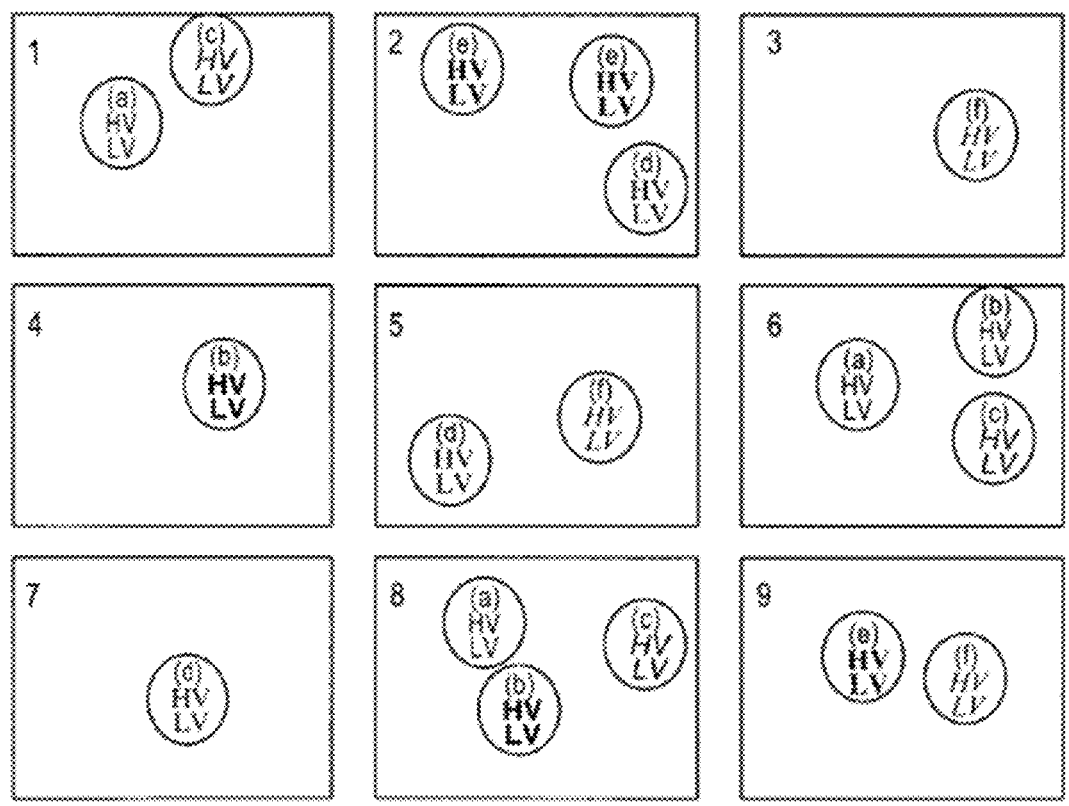
FIG. 4 shows an expanded population of B cells (originating from the population depicted in FIG. 3) divided into nine reaction chambers (vessels).
Figure 5:
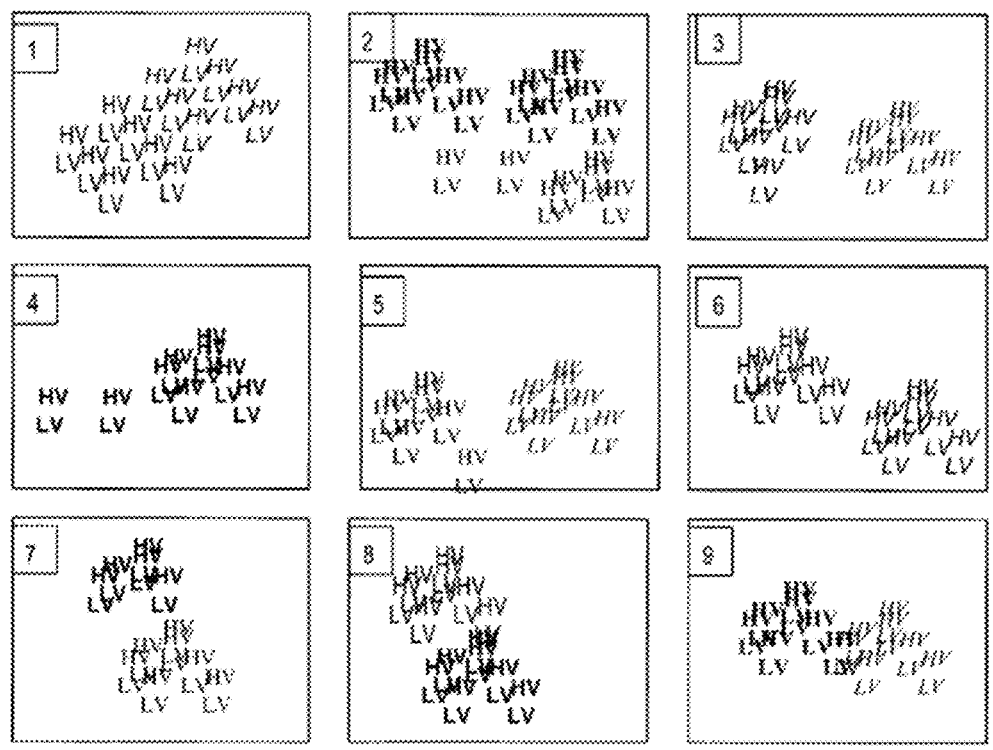
FIG. 5 is a cartoon of the amplified heavy and light chain variable regions from each of the B cells in the nine reaction chambers.

B-cells that may be present in the sample and plurality of lymphocytes include both naïve B-cells and memory B-cells. FIG. 3 is a cartoon depiction of a population of memory B cells (each depicted as a circle), each encoding a unique antibody comprising a heavy chain and a light chain. In one embodiment, the plurality of lymphocytes includes one or more progenitor B-cells, one or more early pro B-cells, one or more late pro-B-cells, one or more pre-B-cells (large or small), one or more immature B-cells, one or more mature B-cells, or a combination thereof. In another embodiment, the plurality of lymphocytes includes one or more marginal-zone B-cells, one or more follicular B cells, or a combination thereof. In another embodiment, the plurality of lymphocytes includes one or more plasma B-cells, one or more memory B-cells, one or more B-1 cells, one or more B-2 cells, one or more regulatory B-cells, or a combination thereof.

An "ASC," as used herein, refers to any cell type that produces and secretes an antibody. Plasma cells (also referred to as "plasma B cells," "plasmocytes" and "effector B cells") are terminally differentiated, and are one type of ASC. ASCs include, for example, activated memory B cells, plasmablasts, cells generated through the expansion of memory B cells, cell lines that express recombinant monoclonal antibodies and hybridoma cell lines.

In one embodiment, the samples described herein comprise one or more lymphocytes and/or one or more antibody secreting cells (ASCs), which in one embodiment is one or more B-lymphocytes. In one embodiment, the plurality of lymphocytes comprises a T-cell or plurality thereof, a B-cell or plurality thereof, an ASC or plurality thereof, or a combination thereof.

Prior to carrying out one of the methods described herein, the plurality of lymphocytes, progenitors thereof, or a combination thereof, can be purified from other cell(s) and sample material. Alternatively, the methods provided herein can be carried out on a sample where the plurality of lymphocytes, progenitors thereof, or a combination thereof has not been purified.

Samples used in the methods described herein are not limited to a specific source or type. Rather any tissue or fluid that may include a population of lymphocytes or progeny thereof may be used herein. For example, in one embodiment, the sample source is a human. In a further embodiment, the human sample is a blood, tissue, tumor (e.g., a tumor biopsy), lymph fluid, bone marrow, epithelial, thymus, lymph gland, lymph node, cerebrospinal fluid (CSF) or peripheral tissue sample. In one embodiment, the sample is a blood, plasma or tissue sample, for example a clinical sample. In one embodiment, the sample comprises a population of T-cells and/or B-cells isolated from the blood or plasma sample. In one embodiment, the sample is a blood sample and in a further embodiment, the blood sample is a peripheral blood mononuclear cell (PBMC) sample. The sample, in one embodiment, is a biopsy, e.g., from liver, lung, colon, kidney, bone marrow, skin or heart. In one embodiment, a sample is a blood sample (e.g., obtained by phlebotomy), biopsy specimen, tissue explant, organ culture, biological fluid or any other tissue or cell preparation from a biological source. In one embodiment, a sample is derived from a solid tissue (e.g., a solid tumor), for example by surgical resection, needle biopsy or other means for obtaining a test biological sample that contains a mixture of cells. The solid sample in one embodiment is mixed with a buffer or water to form a solution or suspension of cells and/or cellular material.

In one embodiment, the source of the sample is a mammal. The sample source in one embodiment is a human. In one embodiment, the sample source is a non-human primate. In a further embodiment, the sample is from a chimpanzee, gorilla, orangutan or baboon. Other sources of samples include, but are not limited to a human, rat, mouse, rabbit, dog, goat, bovine, gerbil, guinea pig, hamster, pig or sheep. In one embodiment, the biological source of the sample is a non-mammalian vertebrate such as an avian or reptilian species.

The present invention is robust in that it is not limited by the number of lymphocytes present in the sample. For example, in one embodiment, from about 50 to about 3,000,000, from about 50 to about 2,500,000, from about 50 to about 2,000,000, or 50 to about 1,500,000, or from about 100 to about 500,000 lymphocytes or progeny thereof can be subjected to the methods of the present invention. In one embodiment, from about 100 to about 10,000, or from about 100 to about 50,000, or from about 1,000 to 100,000, or from about 1,000 to about 80,000, or from about 500 to about 50,000 or from about 500 to about 30,000 or from about 1,000 to about 20,000 lymphocytes or progeny thereof are initially subjected to the methods provided herein.

In one embodiment, the sample comprises a plurality of lymphocytes (e.g., one or more T-cells, B-cells, ASCs (e.g., activated memory B cells), or a combination thereof) from a subject, for example a blood or plasma sample. In one embodiment, the subject is a mammal or vertebrate, e.g., a human. Prior to obtaining the sample, the subject is in one embodiment is immunized or has been immunized with an antigen, according to methods within the ordinary skill in the art. A plurality of lymphocytes can be obtained according to methods within the ordinary skill in the art, for example, via flow cytometry methods. As discussed in further detail below, a sample comprising a plurality of lymphocytes, in one embodiment, is obtained after a selection step based on a functional or binding property, for example, as described in PCT Publication No. WO 2014/153651, which published Oct. 2, 2014, the disclosure of which is incorporated by reference in its entirety for all purposes. In another embodiment, particular memory B cells that express an antibody which binds to an antigen of interest may also be selected by fluorescent activated cell sorting (FACS) using a fluorescently labeled antigen, as is known in the art.

According to one aspect of the invention, a method for identifying a plurality of lymphocyte receptor chain pairs in a sample comprising a plurality of lymphocytes is provided. In another aspect, a method for identifying a functional lymphocyte receptor chain pair in a sample comprising a plurality of lymphocytes is provided. In one embodiment of these aspects, the sample is subjected to conditions suitable for expansion of one or more of the lymphocytes in the sample (FIG. 1, 1001; and FIG. 2, 2001). The conditions suitable for expansion comprise in one embodiment polyclonal activation of lymphocytes. In another embodiment, conditions suitable for expansion comprise antigen-specific activation of specific lymphocytes in the population. Expansion can be carried out by a method or combination of methods known in the art, e.g., for antigen specific activation with multiple antigens/activation compounds, or a combination of polyclonal and antigen specific activation. In one embodiment, conditions suitable for expansion comprise subjecting the plurality of lymphocytes to conditions suitable for cell culture. Expansion of the lymphocytes in the sample, in one embodiment, is used to facilitate the determination of chain pairing from rare lymphocyte clones, as well as to facilitate the selection of subpopulations of functional lymphocytes with desired functional properties, and/or to increase the robustness and sensitivity of lymphocyte receptor chain sequencing.

In one embodiment, one or more activated cells in the expanded sample are purified and/or enriched for. In one embodiment, purification and/or enrichment is carried out to reduce the number of cells to be subsequently tested and to reduce the sequencing depth. Purification/enrichment can be carried out according to methods known to those of ordinary skill in the art. In one embodiment, purification of activated cell(s) is carried out based on identification of cellular morphollogy or expansion marker(s), a FACS secretion assay, purified or enriched, a Milteny kit (e.g IFN-y kit or custom), microfluidic IFN secretion assay (or other relevant cytokine assay), cell marker assay wherein the cell marker is turned on on upon activation, peptide-based purification by FACS, or a combination thereof.

Expansion of lymphocytes in one embodiment, provides a solution to the limitation of determining lymphocyte receptor chain pairing by "co-occurrence." Specifically, if a clone is not represented by a sufficient number of cells (typically about 5) within the sample, it cannot be analyzed by previous methods known to the inventors. In one embodiment, the initial cellular population, e.g., from a human blood sample, is subjected to conditions suitable for expansion that result in at least an average 4-fold expansion of all or a select set of clones within the sample. In one embodiment, the initial cellular population is subjected to culture conditions that result in an average of at least 4-fold expansion, or at least 5-five expansion, or at least 6-fold expansion or at least 7-fold expansion or at least 8-fold expansion of all or a select set of clones within the sample.

Conditions suitable for expansion include both conditions for polyclonal expansion and conditions for antigen-specific expansion.

In one embodiment, the plurality of lymphocytes or progeny thereof, or a subpopulation thereof is activated causing the plurality of lymphocytes or progeny thereof or subset thereof to undergo multiple divisions (FIG. 1, 1001; and FIG. 2, 2001). Activation of the sample therefore leads to the formation of an expanded sample (FIG. 1, 1001; and FIG. 2, 2001). In one embodiment, activation occurs during a cell culture step of the lymphocytes or progeny thereof of the original sample. In one embodiment, in the case of a heterogeneous immune cell population, activation is employed for the entire population of lymphocytes or progeny thereof, e.g., through polyclonal activation, or a subpopulation of cells, e.g., with antigen specific activation and expansion. In one embodiment, where a sample includes a combination of one or more B-cells and one or more T-cells, only the one or more B-cells (or a subpopulation thereof) are activated, only the one or more T-cells (or a subpopulation thereof) are activated, or both the one or more B-cells (or a subpopulation thereof) and the one or more T-cells (or a subpopulation thereof) are activated, and subsequently expanded, to form an expanded sample (FIG. 1, 1001; and FIG. 2, 2001).

Depending on the population of lymphocytes and/or progeny thereof present in the sample, some or all of the population of cells is activated and expanded. In one embodiment, a subpopulation of B-cells in the sample is activated and expanded, or a subpopulation of T-cells in the sample is activated and expanded. In another embodiment, a subpopulation of T-cells and a subpopulation of B-cells in the population are both activated and subsequently expanded to form an expanded sample. Both polyclonal activation and antigen-specific activation are amenable for use with the present methods. Activation and expansion, in one embodiment, occurs in a cell culture step of the lymphocytes or progeny thereof in the sample, or a subpopulation thereof.

Methods for performing antigen-specific expansion of B-cells and T-cells are known in the art and the present invention is not limited by a particular type of method. Rather, the activation step can be carried out according to a protocol determined by the user of the method. Activation of a lymphocyte or progeny thereof causes the activated cell to divide.

B-cells residing primarily in peripheral lymphoid tissues in one embodiment, are activated and expanded into antibody-secreting cells (ASCs) upon antigen stimulation. In vitro, in one embodiment, B-cells are activated under defined culture conditions resulting in polyclonal expansion and differentiation into ASCs. In the case of memory B cells, activation and expansion in one embodiment is accomplished by treating the cells with, for example, Epstein Barr virus, CD40L, or one or more toll like receptor agonists, using protocols that are well known in the art. Protocols described in the literature that may be used to induce B cell activation by adding supplements in the cell culture media are amenable for use with the present invention. These include different combinations of factors such as cytokines (e.g., IL-21, IL-6, IL-4, IL-2, IL-10, IL-15) (Ettinger et al. (2005). The Journal of Immunology 175, pp. 7867-7879; Pinna et al. (2009). Eur. J. Immunol. 39, pp. 1260-1270; Bernasconi et al. (2002). Science 298, pp. 2199-2202) cell surface ligands (e.g., CD40L, BAFF, APRIL), Toll-like receptor agonists (e.g. LPS, CpG, R848, PWM) (Pinna et al. (2009). Eur. J. Immunol. 39, pp. 1260-1270; Boeglin et al. (2011). PLOS One 6, p. e25542. doi:10.1371/journal.pone.0025542; Hartmann and Krieg (2000). J. Immunol. 164, pp. 944-953; Krieg et al. (1995). Nature 374, pp. 546-549; Crotty et al. (2004). J. Immunol. Methods 286, pp. 111-122; Endoh et al. (1987). Cell Immunol. 107, pp. 455-464), monoclonal antibodies against cell surface receptors (e.g. anti-CD40, anti-IgG) (Zhu et al. (2002). J. Immunol. 168, pp. 744-754; Endoh et al. (1987). Cell Immunol. 107, pp. 455-464), and feeder cell lines providing co-stimulation signals (e.g. cell lines expressing CD40L) (Seeber et al. 2014) PLOS One 9, e86184. doi:10.1371/journal.pone.0086184; Wen et al. (1987). Eur. J. Immunol. 17, pp. 887-892; Liebig et al. (2009). J. Vis. Exp. 16, pii: 1373. Doi: 10.3791/1373). Each of the references cited in this paragraph are incorporated by reference herein in their entireties for all purposes.

In the case of T cells, in one embodiment, activation and expansion comprises treatment of the cells with beads that are coated with antibodies against CD3 and CD28 to evoke a polyclonal activation. Polyclonal T cell activation and proliferation can be induced either chemically or by direct cross-linking of T cell receptors (TCR). The most common chemical agents are phorbol 12-myristate 13-acetate (PMA) in combination with ionomycin or phytohaemagglutinin (PHA) activation (Kruisbeek et al. (2004). Curr. Protoc. Immunol. Chapter 3, Unite 3.12. doi: 10.110/0471142735.im0312s60). TCR receptors can be cross-linked by monoclonal antibodies against CD3 and/or CD28 complexes. These antibodies are either immobilized on cell culture plates (Kruisbeek et al. (2004). Curr. Protoc. Immunol. Chapter 3, Unite 3.12. doi: 10.110/0471142735.im0312s60) or coated on beads which are added to T cell cultures (Dynabeads human T-activator CD3/CD28 (Life Technologies, catalog number 1161D)). Alternatively, T cell receptors can be stimulated by irradiated allogeneic peripheral blood mononuclear cells (PBMC) in combination with soluble anti-CD3 mAB (Wick et al. (2014). Clin. Cancer Res. 20, pp. 1125-1134). Cytokines such as IL-2 are often added in the cell culture media to promote further expansion. Each of the references cited in this paragraph are incorporated by reference herein in their entireties for all purposes.

While polyclonal activation is amenable for use in the methods described herein, and can be used to expand rare clones in order to make them amenable to chain pairing analysis, the process expands all clones in the sample and thus is not expected to create a significant enrichment in the relative frequency of any given clone. Thus, when using polyclonal expansion, the total number of immune cells that needs to be analyzed is increased significantly in order to assess chain pairing of the low-abundance clones. In some embodiments, the increased number of cells results in increased cost of sequencing analysis, more complicated and time-consuming bioinformatics analysis, and technical challenges in preparing samples and adequately sampling the resulting amplified materials. Moreover, in one embodiment, polyclonal expansion results in the most abundant clones being over-represented so that they are present in every or the vast majority of containers or wells, upon dividing the activated cells into subpopulations in separate containers or wells. Because the most abundant clones are present in the vast majority or every container, these clones are not amenable to chain pairing analysis. These clones thus encompass a significant fraction of the sequencing reads without providing useful information on pairing.

As the fraction of containers/vessels containing a particular clone decreases below 50%, the ability to predict and assess the pairing of that clone decreases. In the extreme case, a clone that appears only once in the starting pool of cells (maximum frequency of 1/[number of cells in starting sample]) is impossible to pair, as it would appear in only one container. By expanding the starting pool of cells prior to partitioning into a plurality of vessels/containers, additional copies of the clone are generated ($2^{\wedge(number\ of\ divisions)}$). In this regard, upon splitting the population of cells into the plurality of containers, the clone that was originally present as a single cell appears a plurality of times, in multiple containers, to statistically extract the pairing. Accordingly, the present invention addresses the need for methods of identifying low frequency clones. See for example, WO 2014/145992, which discloses the lack of successful pairing of low TCRα and TCRβ mRNA levels leading to the inability to detect certain chain sequences and consequently the ability to pair (WO 2014/145992 at paragraph [00242]).

The inability to extract pairing information of low-frequency clones, without wishing to be bound by theory, is not solely due to the absence of the clone at high enough frequency in the starting population of cells. Rather, the lack of detection (also referred to as "dropout rate") also results from the inability to detect low levels of nucleic acid of a particular chain sequence due to experimental inefficiencies and/or assay sensitivity.

In one embodiment, antigen specific expansion of a T-cell, B-cell and or ASC population is employed to enrich one or more sub-populations of cells, present in the original cell population.

In one embodiment, where the objective is to identify clones with a desired reactivity (e.g., antibody binding one or more of a set of antigens or a T cell recognizing one or more of a set of MHC-peptide complexes) the present invention includes an expansion step that preferentially expands these subsets of clones. When activation and expansion are employed prior to subdividing a cell population into a plurality of vessels or containers (e.g., microwells), the activation and expansion enriches for rare clones with desired reactivity, and generates a sufficient number of representative cells to allow for robust chain pairing analysis by the methods described herein.

The polyclonal and antigen-specific methods described above with respect to expansion of plurality of lymphocytes or progeny thereof, or subset thereof, are also amenable for use on a partitioned population of lymphocytes or progeny thereof (also referred to herein as a subpopulation, a functional subpopulation or functional sub-subpopulation). Accordingly, step 1003 (FIG. 1) and/or 2006 (FIG. 2) can be carried out with the polyclonal and antigen-specific activation and expansion methods described herein, or by another method known to those of ordinary skill in the art.

In the methods described herein, a sample comprising a plurality of lymphocytes or progeny thereof, which is purified or non-purified, or an expanded sample of the same is portioned into individual containers (e.g., individual wells of a microwell plate, individual microfuge tubes). For example, see FIG. 1 at 1002 and FIG. 2 at 2002. As used herein, a "container" is used interchangeably with a "vessel."

For example, in one embodiment, a vessel is an individual well of a multiwell plate. In one embodiment, a 96, 384 or 1536 microwell plate is used to split the cells into individual reaction containers. In one embodiment, the expanded cells are split into 50, 100, 150, 200, 250, 300, 350, 400, 500, 600, 700, 800, 900 or 1000 different reaction chambers for further processing. The number of lymphocytes/progeny thereof, and/or the type of lymphocytes/progeny thereof in each vessel can be the same or different.

In one embodiment, individual single cells from an expanded cell population are divided into distinct containers. In another embodiment, an average of a single lymphocyte or a single lymphocyte progenitor is placed into a plurality of individual containers.

In one prior art method disclosed in WO 2014/145992, a large number of cells are required per container, for example, at least 10,000 cells per container, in order to accurately assess chain pairing for the population of cells in the sample, or a subpopulation thereof. In stark contrast, the present invention allows for a smaller number of initial input of cells per individual container. This necessarily allows for the determination of the pairing of high-frequency clones. Pairing information cannot be extracted from a clone that appears in every container. By using either a small number of starting cells or a range of cell occupancies down to a few cells per container, in one embodiment, determination of chain pairing of almost all high-frequency clones is possible. In the prior art method mentioned above, with 10,000 cells per container, and 96 containers, a starting population of close to a 1,000,000 T-cells or B-cells is required. In many cases, a sample this large is difficult or impossible to obtain (e.g., tumor infiltrating lymphocytes). The present invention therefore allows for the analysis of precious samples.

In one embodiment, as described above, prior to dividing the sample comprising a plurality of lymphocytes or progeny thereof into individual containers, the cells in the sample are activated and expanded (FIG. 1, 1001 and FIG. 2, 2001). In one embodiment, the method step 1001 and/or 2001 is carried out, and a T-cell or B-cell population of approximately 20,000 cells undergoes an average of 4 divisions after activation, the total number of cells (i.e., "expanded population") is 320,000 cells ($2^4 \times 20,000$). Further, each lymphocyte receptor chain pair, in this example, is represented an average of 16 times (assuming 20,000 unique clones in the initial population). It should be understood however that not every clone will be present at the same frequency. Therefore, in other embodiment, each lymphocyte receptor chain pair is not present at the same frequency in the initial population and in this embodiment, each unique chain pair is represented at a minimum of 16 times, on average.

The population of 320,000 cells is partitioned into 100 different containers, each having a total of approximately 3200 cells (FIG. 1, 1002 and FIG. 2, 2002). In one embodiment, the individual containers, or a subset of the individual containers, include a heterogeneous population of cells, i.e., two or more distinct T-cell, B-cell and/or ASC clones. Stated another way, at least one cell within each reaction chamber encodes for an antibody or TCR different from the antibody or TCR encoded by a second cell with the same reaction chamber. Depending on the number of cells, in some embodiments, one or some individual reaction chambers will have zero cells present, or an individual cell present. In one embodiment, the heterogeneous populations of B or T cells may be further cultured after isolation in separate reactors to generate a larger population of cells, possibly including a second activation step (FIG. 1, 1003 and FIG. 2, 2006).

As provided herein, an aspect of the present invention is a method for identifying a plurality of lymphocyte receptor chain pairs in a sample comprising a plurality of lymphocytes or progeny thereof (FIG. 1). In one embodiment of this method, after partitioning the sample (expanded or non-expanded) into individual containers as individual subpopulation (FIG. 1, 1002), one or more of the subpopulations is subjected to an expansion step (FIG. 1, 1003). The expansion in one embodiment is polyclonal expansion. In another embodiment, the expansion is antigen specific expansion. Expansion methods are known to those of ordinary skill in the art and non-limiting examples are provided above. By expanding the one or more subpopulations of cells after partitioning the subpopulations into separate containers, the amount of cellular and nucleic acid material is increased in each expanded subpopulation. This increases the sensitivity of the assay, increases the amount of nucleic acid in the sample and therefore, increases the sensitivity of detection. Upon completion of the expansion step, nucleic acid clonotypes encoding the lymphocyte receptor chains (e.g., mRNA, genomic DNA, cDNA generated from mRNA) in each subpopulation is sequenced to determine the identity of the lymphocyte receptor chains in each subpopulation (i.e., the subpopulation in each individual vessel, see FIG. 1 at 1004).

In one embodiment, where a T-cell, B-cell and/or ASC subpopulation is subjected to an expansion step, each clone of the subpopulation is represented at least four times. Stated another way, where expansion and cell culture is carried out, it is sufficient to provide for at least two divisions, on average, of a single clone originally present in the sample.

Expansion of lymphocytes or progeny thereof after partitioning into subpopulations in one embodiment provides a method to increase the sensitivity of lymphocyte receptor chain pair detection in any given container (vessel) by allowing the cells to expand prior to subjecting them to analysis of their sequences by the co-occurrence approach. This is important for cells that typically have only a small number of mRNA copies for each of the genes of the respective chain pairs. As an example, on average, T-cells have between 3 and 10 copies of each of the alpha and beta receptor chain. Similarly, memory B cells or naïve B cells also typically have low mRNA copy numbers of heavy and light chains. Inefficiencies in methods for amplifying and sequencing TCR or BCR sequences include RNase degradation of transcripts shortly after cell lysis, reverse transcriptase inefficiency, PCR bias and errors, sequencing library construction errors, and cluster generation. In aggregate these inefficiencies can result in less than 10% of the molecules originally present in the sample actually being represented in the final PCR library. If starting from only a few copies in a single cell these inefficiencies and biases often result in no representation for at least one of the chains.

More fundamentally, it is well known that mRNA expression manifests in transcriptional bursts and subsequent mRNA degradation so that, for a given cell at any given time, there is an inherently stochastic nature to the number of mRNA molecules that are present. With mean copy numbers as low as three; many cells will be missed even if all of the technical limitations of amplification described above are overcome. Performing a culture step prior to or after partitioning a sample (see FIG. 1 at 1001, 1003 and FIG. 2 at 2001 and 2006), as described herein, mitigates this problem since each cell will be represented more times, and thus, will have an increased probability of being detected, with both chains present, in a sufficient number of chambers to allow for pairing with statistical significance. Nevertheless, inefficiencies, in certain embodiments, complicate and compromise performance of the assay. To address this problem, in one embodiment, an expansion step after the original cell population is partitioned, into subpopulations, which may or may not have been first expanded, is carried out.

In some embodiments, the exposure of cells to judiciously chosen cell culture conditions will result in a dramatic increase in the expression levels of mRNA for the BCR or TCR chains of interest—an important example of this being the activation of memory B cells to differentiate them into antibody secreting cells. Another benefit of an expansion step following sample partitioning is that the cells are caused to divide and make multiple copies within the well or container. This results in a greater number of total starting transcripts for any given chain and mitigates the inefficiencies and stochastic variability of mRNA expression within any given container. As a result, the detection of paired chains is much more robust. Yet another advantage of a culture step subsequent to partitioning is that it may be used to generate variability in the number of copies of transcripts derived from any clone in the starting sample. This may be done deliberately by selecting expansion conditions that favor some clones or some containers. Nevertheless, even a polyclonal activation will result in some variability of expansion of each of the clones within the sample. This variability in expansion will be observed as variation in read counts for the chains, with paired chains being correlated. This variability may then be used as additional information, beyond statistical increases in co-occurrence between wells, to assist in assigning correct chain pairs.

As provided herein, one aspect of the invention relates to the identification of a functional lymphocyte receptor chain pair that is expressed by a lymphocyte clone, present in a sample comprising a plurality of lymphocytes (i.e., a plurality of unique lymphocyte clones) (see, e.g., FIG. 2).

In many instances, it is desirable to obtain lymphocyte chain pairing information from a clone having a desired functional property, e.g., the sequences of the heavy and light chain of an antibody that binds to a specific target with a specific affinity or specificity, or that is active in a functional assay (e.g., an apoptosis assay), etc. In one embodiment, the methods provided herein enrich the starting population of cells (i.e., from the original sample) or one or more subpopulations of cells (i.e., after placing into separate containers) for a desired property, e.g., a cell that produces an antibody or TCR with a specific target affinity and/or specificity, by the identification of one or more functional subpopulations of cells.

In one embodiment, this method is coupled with functional antibody or TCR analysis using microreactors (e.g., microfluidics), for example, as described in PCT Publication No. WO 2014/153651, which published Oct. 2, 2014, the disclosure of which is incorporated by reference in its entirety for all purposes. For example, in one embodiment, subsample(s) of a sample subpopulation(s), e.g., the cell culture medium from the subpopulation(s) is used in a microfluidic functional assay to measure a property of a lymphocyte receptor chain pair (FIG. 2 at 2003). One or more functional subpopulations are identified based on the results of the assay (FIG. 2 at 2004).

In one embodiment, step 2003 is carried out in the individual vessels in which the sample was partitioned. In another embodiment, step 2003 is carried out in different vessels from which the sample or expanded sample is partitioned. In one embodiment, the functional assay is a microfluidic selection assay and is carried out on one or more subpopulations to identify one or more functional subpopulations (e.g., binding to an antigen). In one embodiment, the functional assay comprises retaining in a plurality of individual vessels a plurality of subpopulations of lymphocytes or progeny thereof, wherein the contents of the individual vessels further comprise a readout particle population comprising one or more readout particles, i.e., for use as a readout mechanism of the particular functional assay. In a further embodiment, the method comprises incubating the individual subpopulations and the one or more readout particles within the individual vessels; assaying the individual subpopulations for the presence of the extracellular effect (functional effect), wherein the readout particle provides a direct or indirect readout of the extracellular effect (functional effect), and determining, based on the results of the assaying step, whether one or more of the subpopulations is a functional subpopulation (FIG. 2 at 2003, 2004). In a further embodiment, the individual vessels are individual microreactors, for example, individual microfluidic chambers. In even a further embodiment, the individual microfluidic chambers are part of a microfluidic structure that includes membrane valves. In one embodiment, the individual vessels are aqueous droplets surrounded by an immiscible fluid such as oil. If a cell or cells in the subpopulation demonstrates the extracellular effect, the subpopulation from which the cell or cells is derived is deemed to be a functional subpopulation (FIG. 2 at 2003, 2004).

In one embodiment of the method shown in FIG. 2, after partitioning the sample or expanded sample into a plurality of containers, a functional analysis is carried out on the plurality of subpopulations (or subsets thereof (e.g., cell culture supernatant), e.g., in different vessels) to identify one or more functional subpopulations of that include a cell that exhibits a desired property (affinity for a particular antigen, specificity for a particular antigen, etc.) (FIGS. 2, 2003 and 2004). Once the functional subpopulation(s) identified, the functional subpopulation(s) is optionally portioned into a second plurality of individual vessels to provide a plurality of functional sub-subpopulations (FIG. 2, 2005). In a further embodiment, one or more of the functional subpopulations or functional sub-subpopulations is subjected to conditions suitable for expansion of one or more of the lymphocytes or progeny thereof in the one or more functional subpopulations or sub-subpopulations to optionally form an expanded subpopulation or expanded sub-subpopulation (FIG. 2, 2006). Methods for expansion are provided above.

The functional assays (FIG. 2, 2003) used in the methods described herein may be varied considerably, according to the desired property the user wishes to identify. In the case of B cells, defined medium conditions may be used to affect a polyclonal expansion and/or differentiation into antibody secreting cells. In such cases assays may be performed on supernatants from these subpopulations to identify functional subsets of B cells, with possible assays including, without limitation, ELISA, ELISPOT, fluorescent binding assays, cell binding assays, neutralization assays, surface plasmon resonance, complement fixation assays, cell-mediated cytotoxicity assays, competition assays, agglutination assays, etc. In one embodiment, a functional assay is performed directly on expanded B cells using methods such as FACS, microscopy, or colony assays. In the case of T-cells, in one embodiment, functional assays include ELISPOT assays of cytokine secretion, FACS analysis to assess binding of TCRs to fluorescently labeled MHC-peptide constructs (e.g., tetramers), cell killing assays, cell proliferation assays, and other assays known to those of ordinary skill in the art.

In one embodiment, the functional assay is performed on a subsample of the subpopulation or plurality thereof, e.g., a sample of supernatant or a portion of cells in the subpopulation, or on the entirety of the subpopulation. Subpopulations may be assayed in a variety of formats. In some instances the expansion of B or T-cells will facilitate the analysis of functional properties within conventional cell culture formats having volumes between ~10 microliters and 10 mL. Formats may also include miniaturized cell analysis reactors including microfluidic devices, microdroplets, open microwells, plates, or semi-solid medium.

In one embodiment, depending on the nature of the functional assay, candidate functional chains are eliminated if present in subpopulations that have been determined to be non-functional. Since this analysis does not rely on the frequency of co-occurrence, it may be performed on both heavy and light chains in the case of BCRs and antibodies, (or alpha, beta, gamma and delta chains for TCRs) independently, or together with correct chain pairing given by the functional heavy and light (or alpha/beta, gamm/delta) pairs obtained. In one embodiment, this approach is used in combination with the co-occurrence approach to further improve the confidence of chain pairing and to provide additional information on the pairing of non-functional antibodies/TCRs.

In one embodiment, the method for determining a chain pair of one or more clones in a population of cells, in one embodiment, is coupled with functional screening and/or binding property screening (e.g., affinity, specificity) using microfluidics, as described in PCT Publication No. WO 2014/153651, which published Oct. 2, 2014, the disclosure of which is incorporated by reference in its entirety for all purposes.

In one embodiment, prior to partitioning the population of lymphocytes or progeny thereof (or expanded sample thereof), into a plurality of subpopulations, the population of cells is sorted based on binding of a biomolecule to one or more cell surface receptors of the cell population. In a further embodiment, only the cells that bind the biomolecule of interest are split into a plurality of different reaction chambers, for further processing.

In one embodiment, the functional assay is one or more functional assays described in PCT Publication No. WO 2014/153651, incorporated by reference herein in its entirety. In another embodiment, the functional assay is a neutralization assay, a serum bactericidal antibody assay (SBA) or an opsonophagocytic assay (OPA). For example, one or more of the functional assays described in Feavers and Walker (2010). Methods Mol. Biol. 626, pp. 199-211, incorporated by reference in its entirety for all purposes, can be used with the methods described herein.

In one embodiment, the functional assay is an ELISA assay.

In another embodiment, the functional assay is a complement dependent cytotoxicity assay (CDC) assay. In another embodiment, the extracellular effect assay is a complement-dependent cytotoxicity (CDC) assay. In one CDC embodiment, a method is provided for identifying the presence of lymphocyte receptor chain pair that binds to a readout cell in the presence of soluble factors necessary and/or sufficient to induce lysis of a readout cell via the classic complement pathway. Accordingly, the assay is to determine whether an antibody secreted by a lymphocyte progenitor stimulates lysis of one or more target cells by the classic complement pathway. Cell lysis by the complement pathway is quantified according to methods known to those of skill in the art. For example, cell lysis is quantified by a clonogenic assay, by the addition of a membrane integrity dye, by the loss of intracellular fluorescent molecules or by the release of intracellular molecules in solution. The released biomolecules are measured directly in solution or captured onto readout particles.

In another embodiment, the functional assay is an antibody-dependent cell mediated cytotoxicity (ADCC) assay. ADCC is a mechanism of cell-mediated immune defense whereby an effector cell of the immune system lyses a target cell, whose membrane-surface antigens have been bound by specific antibodies. Classical ADCC is mediated by natural killer (NK) cells. However, macrophages, neutrophils and eosinophils can also mediate ADCC, and can be provided herein as cells to be used in an ADCC functional assay. ADCC assays are known in the art and components are commercially available. For example, the Guava Cell Toxicity Kit for Flow Cytometry (Millipore), the ADCC Reporter Bioassay Core Kit (Promega), the ADCC Assay (GenScript), the LIVE/DEAD Cell Mediated Cytotoxicity Kit (Life Technologies) and the DELFIA cell toxicity assays can be utilized in the devices provided herein.

A cell growth modulation assay can be performed as a functional assay. The cell growth modulation assay can also be performed with a single readout cell, or a heterogeneous readout cell population in a single chamber, i.e., a readout cell to determine whether cell growth is modulated. The cell growth modulation assay, in one embodiment, is adapted to screen for cells producing biomolecules that inhibit cell growth. In another embodiment, the method is adapted to screen for cells producing molecules that modulate, i.e., increase or decrease, proliferation rates of readout cells. Growth rate, in one embodiment, is measured by manual or automated cell count from light microscopy images, total fluorescence intensity of cell expressing fluorescence, average fluorescence intensity of cells labeled with a dilutive dye (e.g., CFSE), nuclei staining or some other method known to those of skill in the art. Commercially available assay to measure proliferation include the alamarBlue® Cell Viability Assay, the CellTrace™ CFSE Cell Proliferation Kit and the CellTrace™ Violet Cell Proliferation Kit (Life Technologies), each of which can be used with the methods described herein.

In another embodiment, an apoptosis functional assay is carried out to determine a functional subpopulation or functional sub-subpopulation of cells. In one embodiment, the method is used to identify the presence of an antibody that induces apoptosis of a cell.

In one embodiment, an autophagy assay is carried out as the functional assay. In one embodiment, microscopic imaging of the subpopulation(s) is carried out after the assay, to assess autophagy using cell lines engineered with autophagy reporters that are known in the art (e.g., FlowCellect™ GFP-LC3 Reporter Autophagy Assay Kit (U20S) (EMD Millipore), Premo™ Autophagy Tandem Sensor RFP-GFP-LC3B Kit (Life Technologies)).

In one embodiment, a cytokine assay is performed as a functional assay on one or more subpopulations (or subsets thereof). Examples of commercially available cytokine-dependent or cytokine-sensitive cell lines for such assays include, but are not limited to TF-1, NR6R-3T3, CTLL-2, L929 cells, A549, HUVEC (Human Umbilical Vein Endothelial Cells), BaF3, BW5147.G.1.4.OUAR.1, (all available from ATCC), PathHunter® CHO cells (DiscoveRx) and TANGO cells (Life Technologies). A person skilled in the art will understand that primary cells (e.g., lymphocytes, monocytes) may also be used as readout cells for a cytokine assay.

In one embodiment, a signaling assay is used to identify a functional cell subpopulation. Activation of a signaling pathway can be visualized by expression of a fluorescent reporter, translocation of a fluorescent reporter within a cell, a change in growth rate, cell death, a change in morphology, differentiation, a change in the proteins expressed on the surface of the readout cell, etc. Several engineered reporter cell lines are commercially available and can be used to implement such an assay. Examples include PathHunter Cells® (DiscoverRx), TANGO™ cells (Life Technologies) and EGFP reporter cells (ThermoScientific).

In one embodiment, a virus neutralization assay is carried out as a functional assay, e.g., to assess whether a lymphocyte receptor chain pair is present that interferes with the ability of a virus to infect a target cell. Assessment of viral infection may be done using methods known in the art. For example, the virus can be engineered to include fluorescent proteins that are expressed by the readout cell following infection, the expression of fluorescent proteins within the readout cell that are upregulated during viral infection, the secretion of proteins from a readout cell or accessory cell, which are captured and measured on readout particles that are increased during viral infection, the death of the of a readout cell or accessory cell, the change in morphology of a readout cell or accessory cell, and/or the agglutination of readout cells.

In one embodiment, the functional assay measures binding of a lymphocyte receptor chain pair to a cell surface protein or membrane bound or integral membrane receptor, such as a G-protein coupled receptor. In another embodiment, the functional assay measures the activation of a cell signaling protein or the phosphorylation of a target protein.

As provided above, the methods provided herein can be coupled to microfluidic analysis in order to perform one or more functional assays (FIGS. 2, 2003 and 2004), on a sample subpopulation or expanded sample subpopulation, or subsample (subportion, e.g., cell culture medium). In certain embodiments, the microfluidic devices provided herein are based on Multilayer Soft Lithography (MSL) microfluidics (Unger et al. (2000). *Science* 7, pp. 113-116, incorporated by reference in its entirety). MSL is a fabrication method that provides for increased sensitivity through small volume reactions; high scalability and parallelization; robust cell culture; flexibility and fluid handling control needed for complex assays; and greatly reduced cost and reagent consumption.

The number of cells isolated per device run (i.e., number of cells in each chamber of a device) is a function of the concentration of cells in a cell suspension loaded onto a device, the frequency in the cell suspension of the specific cell(s) being selected for, and the total number of chambers on a device. Devices with arrays up to and greater than 40,000 cell assay chambers are contemplated.

Rather, in one aspect, functional lymphocyte receptor chain pairs are determined via statistical enrichment. This approach can be used in lieu of determination of chain pairs by co-occurrence, or as a complementary approach. This aspect is based on the statistical analysis of the frequency of appearance of chains within functional populations identified as containing cells with a desired functional property, as compared to their frequency of appearance within populations that have been identified as not testing positive for the same functional property.

Some or all of a functional subpopulation containing a functional clone (corresponding to the functional property), where the clone comprises a number N of cells, is divided into M sub-subpopulations (FIG. 2, 2005), with M selected to be such that the distribution of cells from the clone with the desired property is limiting and well-described by a binomial distribution across the sub-subpopulations. The sub-subpopulations are then optionally expanded again (FIG. 2, 2006). The sub-subpopulations are further assayed to determine which contain a lymphocyte receptor chain pair and therefore, a lymphocyte cell or progenitor thereof, with the desired property, and which do not (i.e., the functional assay is performed on the sub-subpopulations). Following this functional analysis of the sub-subpopulations, each sub-subpopulation (functional and non-functional) is analyzed via a sequencing assay to determine the sequences of all the lymphocyte receptor chains (e.g., TCR α, β chains γ, δ chains, heavy and light chains of antibody or BCR, or a combination thereof) that are produced in the respective sub-subpopulations. For each of the chains identified within the "functional" sub-subpopulations, the frequency of detection within functional and non-functional subpopulations is determined to identify chains that are statistically enriched in the functional sub-subpopulations. These chains are assigned a p-value representing the likelihood that the observed frequencies of occurrence between the functional and non-functional population occur by chance.

In one embodiment, depending on the nature of the functional assay, candidate functional chains are eliminated if present in sub-subpopulations that have been determined to be non-functional. Since this analysis does not rely on the frequency of co-occurrence, it may be performed on both heavy and light chains in the case of BCRs and antibodies, or alpha, beta, gamma and delta chains for TCRs, independently, or together with correct chain pairing given by the functional lymphocyte receptor chain pairs obtained. In one embodiment, this approach is used in combination with the co-occurrence approach to further improve the confidence of chain pairing and to provide additional information on the pairing of non-functional lymphocyte receptor chains.

In one embodiment, a functional assay is carried out microfluidically. Amongst all microfluidics technologies, MSL is unique in its rapid and inexpensive prototyping of devices having thousands of integrated microvalves (Thorsen et el. (2002). *Science* 298, pp. 58-584, incorporated by reference in its entirety). These valves can be used to build higher-level fluidic components including mixers, peristaltic pumps (Unger et al. (2000). *Science* 7, pp. 113-116) and fluidic multiplexing structures (Thorsen et el. (2002). *Science* 298, pp. 58-584; Hansen and Quake (2003). *Curr. Opin. Struc. Biol.* 13, pp. 538-544, incorporated by reference in their entireties herein) thus enabling high levels of integration and on-chip liquid handling (Hansen et al. (2004). *Proc. Natl. Acad. Sci. U.S.A.* 101, pp. 14431-1436; Maerkl and Quake (2007). *Science* 315, pp. 233-237, each incorporated by reference in their entireties).

Figure 7:
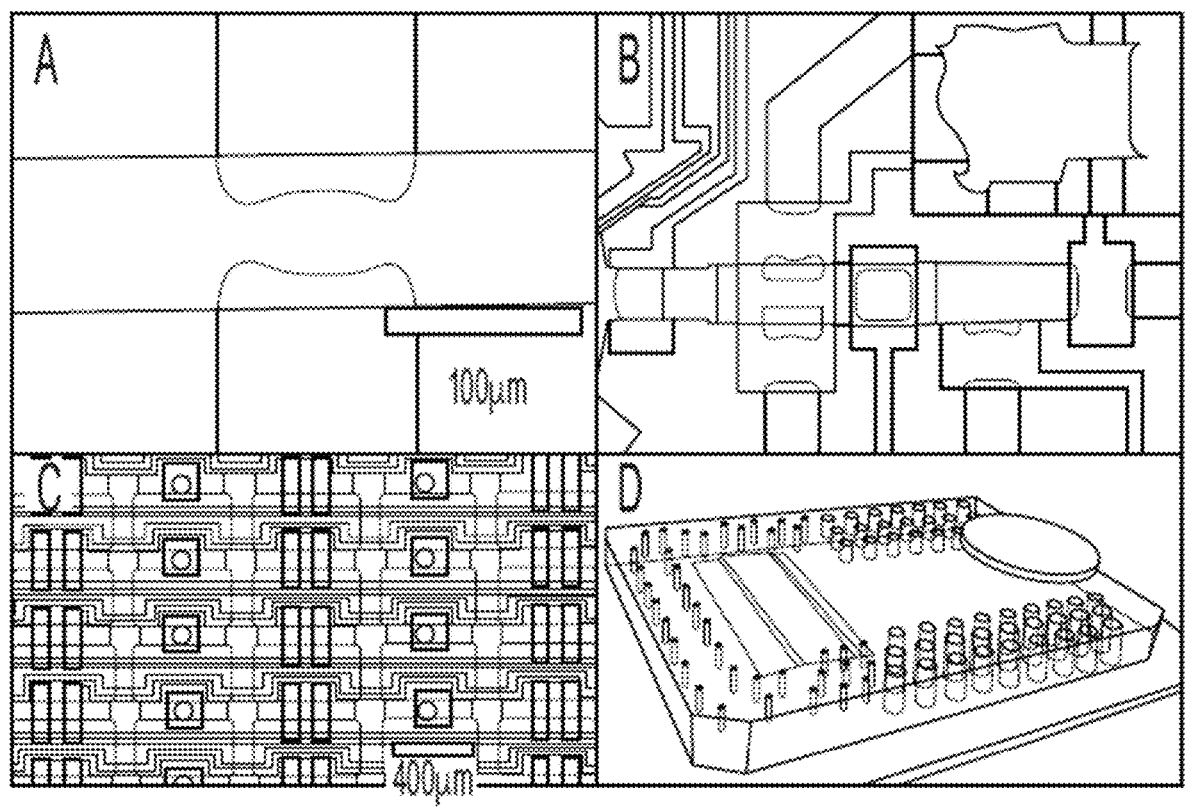
FIG. 7 provides images showing various aspects of multilayer soft lithography microfluidics. (A) Optical micrograph of a valve made using multilayer soft lithography (MSL). Two crossing microfabricated channels, one "flow channel" for the active fluids (vertical) and one control channel for valve actuation (horizontal), create a valve structure. The flow channel is separated from the control channels by a thin elastomeric membrane to create a "pinch valve". Pressurization of the control channel deflects the membrane to close off the flow channel. (B) Section of a device integrating multiple valves (filled with green and blue food dye). (C) Section of a device having a total of 16,000 valves, 4000 chambers, and over 3000 layer-layer interconnects (arrow). (D) Example of a microfluidic device with penny for scale.

FIG. 7A shows an optical micrograph of a valve made by MSL. Two crossing microfabricated channels, one "flow channel" for the active fluids (vertical) and one control channel for valve actuation (horizontal), create a valve structure. The flow channel is separated from the control channels by a thin elastomeric membrane to create a "pinch valve." Pressurization of the control channel deflects the membrane to close off the flow channel. FIG. 7B shows a section of an MSL device integrating multiple valves (filled with green and blue food dye). FIG. 7C is a section of a device having a total of 16,000 valves, 4000 chambers, and over 3000 layer-layer interconnects (arrow). FIG. 7D shows an example of a microfluidic device with penny for scale. Devices shown are for illustration of one embodiment of the MSL fabrication technology.

The assay chambers of a device, in one embodiment, have an average volume of from about 100 pL to about 100 nL. For example, in one embodiment, one or more properties of an effector cell is assayed within a microfluidic chamber comprising a cell population wherein the volume of the microfluidic chamber is about 100 pL, about 200 pL, about 300 pL, about 400 pL, about 500 pL, about 600 pL, about 700 pL, about 800 pL, about 900 pL or about 1 nL. In another embodiment, the volume of the microfluidic chamber is about 2 nL. In another embodiment, the volume of the microfluidic chamber for assaying a property of an effector cell in a cell population is from about 100 pL to about 100 nL, from about 100 pL to about 50 nL, from about 100 pL to about 10 nL, from about 100 pL to about 1 nL, from about 50 pL to about 100 nL, from about 50 pL to about 50 nL, from about 50 pL to about 10 nL or from about 50 pL to about 1 nL. In even another embodiment, the volume of the microfluidic chamber for assaying a property of an effector cell in a cell population is about 10 nL, about 20 nL, about 30 nL, about 40 nL, about 50 nL, about 60 nL, about 70 nL, about 80 nL, about 90 nL or about 100 nL.

The MSL fabrication process takes advantage of well-established photolithography techniques and advances in microelectronic fabrication technology. The first step in MSL is to draw a design of flow and control channels using computer drafting software, which is then printed on high-resolution masks. Silicon (Si) wafers covered in photoresist are exposed to ultraviolet light, which is filtered out in certain regions by the mask. Depending on whether the photoresist is negative or positive, either areas exposed (negative) or not (positive) crosslinks and the resist will polymerize. The unpolymerized resist is soluble in a developer solution and is subsequently washed away. By combining different photoresists and spin coating at different speeds, silicon wafers are patterned with a variety of different shapes and heights, defining various channels and chambers. The wafers are then used as molds to transfer the patterns to polydimethylsiloxane (PDMS). In one embodiment, prior to molding with PDMS and after defining photoresist layers, molds are parylene coated (chemical vapor deposited poly(p-xylylene) polymers barrier) to reduce sticking of PDMS during molding, enhance mold durability and enable replication of small features In MSL, stacking different layers of PDMS cast from different molds on top of each other is used to create channels in overlapping "flow" and "control" layers. The two (or more) layers are bound together by mixing a potting prepolymer component and a hardener component at complementary stoichiometric ratios to achieve vulcanization. In order to create a simple microfluidic chip, a "thick" layer (e.g., between from about 200-2000 μms) is cast from the mold containing the flow layer, and the "thin" layer (e.g., between from about 25 to about 300 μms) is cast from the mold containing the control layer. After partial vulcanization of both layers, the flow layer is peeled off its mold, and aligned to the control layer (while still present on its mold, by visual inspection. The control and flow layers are allowed to bond, for example at 80° C. for about 15-60 minutes. The double slab is then peeled from the control mold, and inlet and outlet holes are punched and the double slab is bonded to a blank layer of PDMS (i.e., a flat layer of PDMS with no structural features). After allowing more time to bond, the completed device is mounted on a glass slide. Fluid flow in the device is controlled using off-chip computer programmable solenoids which actuate the pressure applied to fluid in the channels of the control layer. When pressure is applied to these control channels, the flexible membrane between the overlapping orthogonal control and flow lines deflects into the flow channel, effectively valving the flow. Different combinations of these valves can be used to create peristaltic pumps, multiplexer controls and isolate different regions of the chip With respect to the flow layer, assay chambers and channels for controlling fluidic flow to and from the assay chambers are defined by the photoresist layers. As will be appreciated by one of skill in the art, the thickness of a photoresist layer can be controlled in part by the speed of spin coating and the particular photoresist selected for use. The bulk of the assay chambers, in one embodiment, are defined by an SU-8 100 feature which sits directly on the Si wafer. As known to those of skill in the art, SU-8 is a commonly used epoxy-based negative photoresist. Alternatively, other photoresists known to those of skill in the art can be used to define assay chambers with the heights described above. In some embodiments, the assay chambers have a height and width of 50-500 µM and 50-500 µM, respectively, as defined by the SU-8 features.

Figure 8:
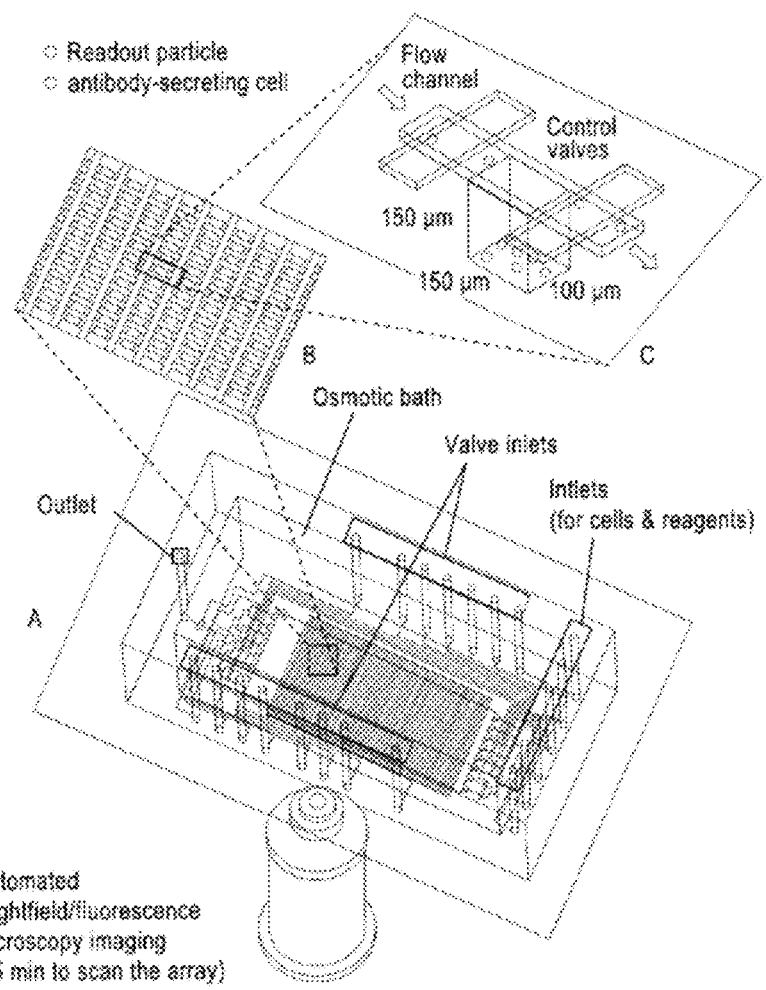
FIG. 8 is a schematic of one device amenable for microfluidic screening of T cells or ASCs. (A) Schematic showing the structure of a microfluidic device for antibody selection from single antibody-secreting cells. (B) Array of 4,032 analysis chambers. Each chamber is isolated during incubation and media can be exchanged within minutes. (C) Close up of an individual chamber. Cells, readout particles and reagents are injected sequentially, settling down by gravity. Imaging is performed using automated brightfield/fluorescence microscopy.

MSL fabrication techniques allow for a wide range of device densities, and chamber volumes to be fabricated. For the devices provided herein, in one embodiment, from about 2000 to about 10,000 T cell and/or ASC analysis chambers are provided in a single integrated device. The T cell and/or ASC cell analysis chambers, in one embodiment, have an average volume of from about 1 nL to about 4 nL, for example, from about 1 nL to about 3 nL, or from about 2 nL to about 4 nL. The T cell and/or ASC cell analysis chambers, in one embodiment, are connected in a serial format, as depicted in FIG. 8. For example, a device with 4032 individual analysis chambers (average volume of 2.25 nL) connected in serial format achieve a screening throughput of approximately 100,000 cells per run, as described in PCT Publication No. WO 2014/153651, which published Oct. 2, 2014, incorporated by reference in its entirety for all purposes. The integrated microfluidic valves harnessed in the devices provided herein allow for chamber isolation, and programmable washing with reagents selected from a plurality of inlets, for example from 2 to about 32 inlets, 2 to about 20 inlets, 2 to about 15 inlets, 2 to about 10 inlets, or from 2 to about 9 inlets, or from 2 to about 8 inlets, or from 2 to about 7 inlets or from 2 to about 6 inlets. Additional inlets are provided to control valve pressure (FIG. 8).

Figure 9:
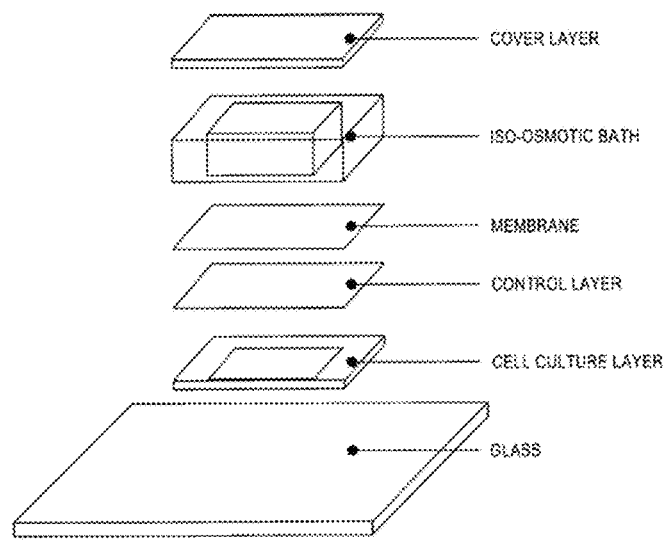
FIG. 9 is a schematic of the layers that are assembled during one embodiment of device fabrication.

Importantly, when microfluidic analysis is coupled to the sequencing and statistical methods provides herein, the devices allow for the long term culture and maintenance of cells. Microfluidic arrays of chambers are fabricated within a thick membrane (e.g., from about 150 µm to about 500 µm thick, about 200 µm thick, about 300 µm thick, about 400 µm thick or about 500 µm thick) of PDMS elastomer that is overlaid a reservoir of medium, for example 1 mL of medium as described previously (Lecault et al. (2011). Nature Methods 8, pp. 581-586, incorporated by reference herein in its entirety for all purposes). The proximity of the medium reservoir (osmotic bath) to the cell chambers effectively blocks evaporation (through the gas-permeable PDMS material) and ensures robust cell viability and where cells are not fully differentiated, growth over several days, and is critical for achieving long-term culture in nL volumes with growth rates and cellular responses that are identical to microliter volume formats. FIG. 9 shows a schematic of the layers of an embodiment of one of the devices provided herein.

Microfluidic analysis, in one embodiment, is carried out to identify a population of ASCs and/or T cells comprising one or more cells that exhibit a particular functional or binding property. For example, microfluidic analysis can be used to obtain an ASC population or T cell population that binds to a particular receptor or antigen associated with a disease or infectious agent.

Once identified, the population(s) are recovered and subjected to the methods described herein for chain pairing analysis.

Recovery, in one embodiment, comprises piercing the microfluidic chamber comprising the cell population comprising the one or more cells that exhibit the extracellular effect, with a microcapillary and aspirating the chamber's contents or a portion thereof to obtain a recovered aspirated cell population. Various methods for the recovery of one or more cells from a specific chamber(s) are amenable for use herein.

Figure 10:
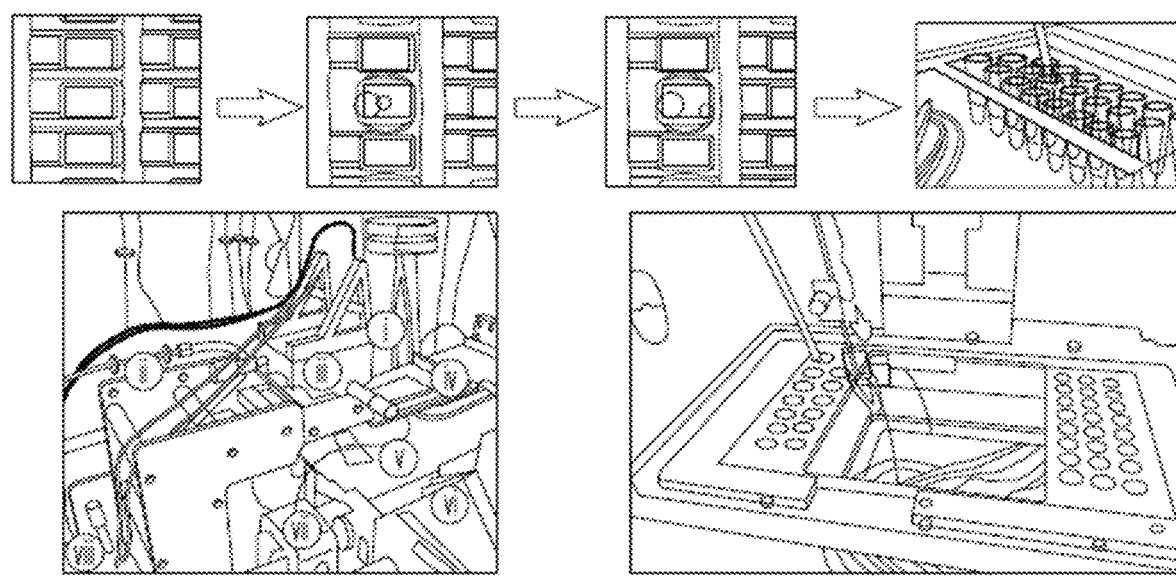
FIG. 10 shows images of a microfluidic instrument for cell recovery and an image sequence during cell recovery. Top: From left to right. Optical micrograph of image sequence during cell recovery with cells in chamber, capillary piercing chamber roof (far left), empty chamber following aspiration, and capillary dispensing cells into tube (far right). Bottom left: Image of custom-built microfluidic screening instrument including (i) microcapillary mounted on robotic micromanipulator, (ii) digital pneumatics for nanoliter flow aspiration/dispensing, (iii) X-Y translation mount, (iv) incubator insert with mounts for recovery tubes, (v) scanning X-Y stage for image acquisition across the array, (vi) inverted microscope, (vii) cooled Hamamatsu CCD camera for high-sensitivity fluorescent imaging, and (viii) control solenoids for capillary operation. Bottom right: Close up of microfluidic device mounted beneath incubator insert with capillary positioned for cell recovery.

The PDMS membrane design of the devices provided herein enables the selective recovery of cells from any chamber by piercing the upper membrane with a microcapillary. In one embodiment, cell recovery from a chamber is carried out based in part on the methods set forth by Lecault et al. (2011). Nature Methods 8, pp. 581-586, incorporated by reference herein in its entirety for all purposes. The membrane above a particular chamber is pierced with the microcapillary and cells are aspirated (FIG. 10, top). The same microcapillary can be used to recover multiple cell populations on one device. Recovered cells can then be deposited in microfuge tubes for further analysis, as described herein.

In one embodiment, one or more cell populations are recovered with a microcapillary by aspirating the contents of the chamber(s) containing the cell population(s) to provide a recovered aspirated cell population. The recovered aspirated cell population is then subjected to the chain pairing analysis methods provided herein.

Recovery, in one embodiment is automated and using a robotic microcapillary instrument (FIG. 10, bottom right). However, recovery can also be accomplished manually with a microcapillary. The recovery methods provided herein allow for the recovery from 100 chambers with >95% efficiency in 15 minutes.

A microcapillary, as stated above in one embodiment, is used to recover one or more cell populations from a microfluidic chamber. The cells in the one or more cell populations are substantially recovered by aspirating the chamber contents into the microcapillary, to provide a recovered aspirated cell population. The microcapillary in one embodiment, has a diameter of from about 5 µm to about 200 µm. In a further embodiment, the microcapillary has a diameter of from about 5 µm to about 200 µm, or from about 5 µm to about 150 µm, or from about 5 µm to about 100 µm, or from about 5 µm to about 75 µm, or from about 5 µm to about 50 µm, or from about 50 µm to about 200 µm, or from about 100 µm to about 200 µm, or from about 150 µm to about 200 µm.

In some embodiments, the microcapillary has a beveled tip. In some embodiments, the microcapillary has an oval, square or circular cross section. Additionally, as shown in FIG. 10, the microcapillary in some embodiments is mounted on a robotic micromanipulation system on a microscope to provide an automated recovery apparatus.

In one embodiment, the microcapillary provided herein has a single barrel. However, the microcapillary in other embodiments has multiple barrels, for example a double barrel, a triple barrel, or more than three barrels.

In one embodiment, the contents of a chamber comprising an effector cell displaying a variation in an extracellular effect are recovered from the device by aspiration, for example, by using a microcapillary fabricated to have an appropriate size and shape. In some embodiments, the recovery method comprises piercing the top of the chamber comprising the cell(s) of interest with the microcapillary and aspirating the cell(s) of interest. In one embodiment, the membrane reseals or substantially reseals after piercing is complete. In another embodiment, recovery of the contents of a chamber comprising an effector cell displaying a variation in an extracellular effect (e.g., one or more ASCs) is performed by first cutting a wall of the chamber to create an access point and then extracting cells by aspiration using a microcapillary. In yet another embodiment, the microfluidic device used to assay the extracellular effect is fabricated such that the chambers are exposed by peeling away the material on one wall, thereby leaving an open micro-well array. Identified chambers (i.e., chamber(s) comprising an effector cell displaying a variation in an extracellular effect) are then aspirated from their respective chambers. In order to facilitate the precise extraction of microfluidic well contents, aspiration tools such as microcapillary tubes, in one embodiment, are mounted on a robotic micromanipulator, or a manual micromanipulator (FIG. 10). However, aspiration in other embodiments is performed manually.

Recovery of one or more cells from one or more microfluidic chambers, in one embodiment, comprises magnetic isolation/recovery. For example, in one embodiment, a microfluidic chamber is exposed to a magnetic particle (or plurality of magnetic particles) that adheres to the one or more cells within the chamber. Adherence can be either selective for a single cell, a sub-population of the population of cells in the well(s), or non-selective, i.e., the magnet can adhere to all cells. In this case, instead of aspirating cells into a micro-capillary, cells labeled with magnetic particles are drawn to a magnetic probe that creates a magnetic field gradient. The probe, in one embodiment, is designed to enable the magnetic field to be turned on and off, causing cells to adhere to it for removal and then be released during deposition. (EasySep Selection Kit, StemCell Technologies).

In the methods described herein for identifying a plurality of lymphocyte receptor chain pairs in a sample comprising a plurality of lymphocytes or progeny thereof, nucleic acid encoding the lymphocyte receptor chains in each subpopulation is sequenced (for example, genomic DNA, mRNA or cDNA) (FIG. 1 at 1004). Sequencing can be carried out specifically on the nucleic acid encoding the lymphocyte receptor chain pairs, or a whole transcriptome approach can be carried out on the mRNA expressed in the respective subpopulations. In this embodiment, the mRNA is first reverse transcribed to cDNA prior to sequencing. As provided below, an amplification step can be carried out prior to sequencing. However, amplification is not required by the methods provided herein.

In the methods described herein for identifying a functional lymphocyte receptor chain pair in a sample comprising a plurality of lymphocytes or progeny thereof, nucleic acid encoding the lymphocyte receptor chains in each subpopulation are sequenced (FIG. 2 at 2007).

The nucleic acid used for sequencing can be either genomic DNA or messenger RNA. Moreover, an amplification step is not required prior to sequencing the nucleic acid. In some instances, because of the inefficiencies associated with amplification, it is desirable to directly sequence the nucleic acid without an amplification step. Previously described methods for identifying lymphocyte receptor chain pairs in a sample each require amplification. Amplification in some embodiments introduces deleterious amplification artifacts including PCR errors, the formation of chimeric amplification products, unwanted side-products, unwanted amplification of pseudogenes, and the potential for large bias in the efficiency of different amplicons. Accordingly, in one embodiment as described herein, amplification of nucleic acid is not carried out, and instead, one or more cell expansion steps (either prior to or subsequent to portioning) is carried out. In these embodiments, natural cell division and DNA replication is harnessed to produce sufficient material for sequencing. In some embodiments, cell expansion is used together with nucleic acid amplification, but the number of nucleic acid amplification rounds is significantly reduced, as compared to the rounds required without a cell expansion step. In one embodiment, cell expansion is conducted to a sufficient extent to completely eliminate any need for nucleic acid (e.g., PCR) amplification. In a further embodiment, direct sequencing analysis of RNA is performed by generating cDNA, performing a second strand synthesis, and then ligating on suitable sequencing adapters and indexes. In another embodiment, direct sequencing of genomic DNA is carried out. In a further embodiment, genomic DNA is purified from each subpopulation followed by direct construction of indexed shot-gun sequencing libraries, optionally followed by enrichment of regions coding for lymphocyte receptor chain nucleic acid, e.g., antibody or TCR genes.

In one embodiment, a barcoding approach is employed wherein each barcode is attached to nucleic acid of distinct subpopulations (e.g., each functional subpopulation, sub-subpopulation. In a further embodiment, reverse transcription (RT) is performed using primers specific for the lymphocyte chain pairs (e.g., alpha and beta constant-region primers, delta and gamma constant region primers) and an M-MLV (Moloney Murine Leukemia Virus), or M-MLV derived Reverse Transcriptase (RT). A 5' priming site is then added by template switching. The template switching oligonucleotide in one embodiment, contains a unique molecular identifier (barcode) which allows for bioinformatic distinction of true diversity from PCR and sequencing errors. PCR is carried out using forward and reverse primers containing 6 bp indexes and sequences complementary to the sequencing flow cell adapters, eliminating the need for standard library preparation. Pooled libraries are in one embodiment, purified using a combination of Ampure XP beads and agarose gels, quantified by qPCR, and sequenced. In a further embodiment, sequencing is carried out on an Illumina MiSeq with paired end 2×300 bp reads.

As provided above, in one embodiment, once the sample is partitioned into separate containers as subpopulations, the nucleic acid present in the subpopulations or identified functional subpopulations (or sub-subpopulations) is subjected to a sequencing assay. Nucleic acid (e.g., messenger RNA or genomic DNA) in one embodiment is subjected to direct library preparation for sequencing, or amplified, followed by library preparation of the amplicons for sequencing, for example, using the Illumina Nextera protocol (catalog no. FC-121-1031), incorporated by reference in its entirety herein.

In one embodiment, in each individual vessel, the subpopulation(s) are lysed and nucleic acid from the lysed cells are amplified.

In one embodiment, a unique molecular identifier (barcode) sequence is added to the nucleic acid from the lysed cells. The index sequence can be attached either before, during, or after amplification of the nucleic acid sequences and may be attached to the 5' and/or 3' end of the nucleic acid (genomic DNA, cDNA, RNA, mRNA), or to an internal region of the nucleic acid. For example, the index sequence in one embodiment, comprises a sequence complementary to the 5' region of the nucleic acid. In another embodiment, the index sequence comprises a sequence that is complementary to the 3' region of the nucleic acid. In one embodiment, the nucleic acid comprises RNA, and the RNA is digested and the index sequence is attached to the fragmented RNA. In one embodiment, the barcode sequence is attached to cDNA. In a further embodiment, the index sequence hybridizes to the polyA tail of the mRNA. In another embodiment, genomic DNA is fragmented and the barcode sequence is attached to the fragmented DNA. In one embodiment, index sequences are attached only to antibody sequences. In another embodiment, index sequences are only attached to TCR sequences. However, in another embodiment, barcode sequences are attached non-specifically to the nucleic acid in the sample. A barcode sequence, in one embodiment, comprises an amplification primer or a region complementary to a binding site for an amplification primer. Alternatively, a barcode sequence is attached to the nucleic acid via one or more ligation (blunt-end and/or sticky end) reactions.

In one embodiment, attachment of a barcode sequence comprises attachment to an RNA molecule, e.g., an mRNA molecule. The barcode sequence in one embodiment, comprises a sequence that acts as a primer for a reverse transcription reaction. For example, the index sequence, in one embodiment, comprises an oligodT sequence that hybridizes to the polyA tail of an mRNA molecule. The oligodT portion of the index sequence acts as a primer for first strand synthesis of the cDNA molecule.

The length and composition of barcode sequences can vary depending on the number of subpopulations or functional subpopulations (or sub-subpopulations).

In one embodiment, before or after the barcode sequences are added, the nucleic acids are amplified in one reaction, e.g., by a polymerase chain reaction (PCR), e.g., an RT-PCR reaction. Amplification of the nucleic acids can comprise PCR-based methods or non-PCR based methods. As provided above, a barcode sequence can be added before, during or after amplification. Amplification, in one embodiment, comprises exponential amplification of the nucleic acids. In another embodiment, amplification comprises linear amplification of the indexed sequences (e.g., RNA amplification by in vitro transcription). In one embodiment, amplification comprises isothermal amplification such as rolling circle amplification. In some instances, amplification of the nucleic acid comprises non-PCR based methods. Examples of non-PCR based methods include, but are not limited to, nucleic acid sequence-based amplification (NASBA), strand displacement amplification (SDA) (real time or non-real time), multiple displacement amplification (MDA), transcription-mediated amplification (TMA), rolling circle amplification, or circle-to-circle amplification. Methods for performing the aforementioned amplification methods can be implemented according to known protocols to those of ordinary skill in the art.

Barcode sequences can be added to the amplification products after amplification or can be added during amplification, as provided above. The barcoded sequences are then pooled and sequenced, for example, on a next-generation or third generation sequencer. Sequencing reactions can be carried out on all or substantially all of the indexed nucleic acid sequences. In one embodiment, a sequencing-by-synthesis reaction is carried out on all the indexed nucleic acid sequences. In another embodiment, a sequencing-by-synthesis reaction is carried out on substantially all of the indexed nucleic acid sequences. In one embodiment, a SMRT® (Pacific Biosciences of California) sequencing is employed on all or substantially all of the indexed nucleic acid sequences. In another embodiment, a FRET-based approach (e.g., VisiGen Biotechnologies, Houston, Tex.) or a nanopore nucleic acid sequencing approach (Gupta (2008). Trends in Biotechnology 26, pp. 602-611, incorporated by reference herein in its entirety) is employed on substantially all of the indexed nucleic acid sequences. As provided above, index sequences can be added to the entirety of a nucleic acid pool (e.g., all of the mRNA or genomic DNA in a sample) or a portion thereof (e.g., only the antibody sequences or TCR sequences).

In one embodiment, whole transcriptome amplification is carried out for the identification of lymphocyte receptor chain sequences without primers specific to the lymphocyte receptor chains. One embodiment of this method is described below. See also FIGS. 19-20.

Cell subpopulations or sub-subpopulations are processed using a modified version of a protocol described in the literature for single cell RNA-seq using a "template switching" approach. Briefly, samples are lysed in a buffer containing a certain concentration of polyT primer flanked with a universal sequence and reverse transcription is performed using Maxima RNaseH-reverse transcriptase in the presence of a template switching primer. PCR amplification of the resulting cDNA products is performed (e.g., with Kappa master mix) with a primer complimentary to the universal sequence added to the polyT and template switching primer. PCR is then carried out. For example, the total number of PCR cycles can be varied, e.g., between 17 and 25 depending on both the size of the cells and/or total number of cells in each subpopulation or sub-subpopulation. PCR products are then purified, for example, with Ampure XP beads.

Library preparation is performed on each sample following Illumina's Nextera XT protocol. Each double stranded DNA subpopulation or sub-subpopulation are fragmented and indexed into ~350 bp population fragments using a transposase based approach. Samples are then pooled together and purified using Ampure Xp beads. Sequencing is performed, for example on an Illumina platform (MiSeq/NextSeq). In one embodiment, a paired end 2×300 bp read length is used and raw reads are assigned to the initial samples based on the indexes used during library preparation. In addition to providing information about the transcriptome of each sample, lymphocyte receptor chain pairs are assembled using a custom based script written in Matlab. For example, in the case of a heavy and light chain antibody sequence, single and paired end reads are first trimmed based on quality. Then, sequences corresponding to the constant region of each immunoglobulin isotype (IgG, IgA, IgM, IgE) and light chains are used as template to align the reads from each sample. Once some reads are assembled to the initial seed template, the script finds the next consensus region using a pre-defined value for coverage and repeats the process until no more reads align, typically covering the entire variable region as well as the leader sequence. This approach allows the assembly of heavy and light chain antibody sequences with high efficiency without the need to use gene specific antibody primer mixes. Further, due to the diversity of sequences within the variable regions of antibody or TCR genes, this assembly process may be used to recover multiple TCR or antibody chains from a single sample comprised of pooled fragments of the resulting amplified cDNA product. In some instances the number of unique chain pairs may be approximately 10, 100, or 1000. This approach further has the advantage that it may be applied equally to the analysis of antibody or TCR sequences from any species without the need to redesign and/or optimize primer sequences. This approach also has the advantage that it allows for capture of all isotypes of antibodies without the need for multiplexed primer sets that may result in amplification bias, missed sequences, and the introduction of errors in the sequence due to mispriming of degenerate primers. Finally, this approach preserves the full leader sequence of antibody and/or TCR chains so that they may be used in final cloning and expression. FIGS. 20 and 21 show the result of this method. FIG. 20 is a graphical example of the assembly process using reads obtained from a next generation sequencing run (SEQ ID NOs: 1-21). Reads are aligned to a template sequence corresponding to a conserved region on the constant region for both heavy and light chains respectively and extend toward the variable region by aligning additional reads to newly generated consensus sequence. This iterative process allows the assembly of heavy and light chain antibody sequences covering the entire variable region as well as leader sequences for each individual sequence.

One aspect of the invention relates to lymphocyte receptor chain nucleic acid sequencing where no barcode is added to subpopulations or sub-subpopulations. In this aspect, a fusion/linkage based demultiplexing approach is carried out in a method to determine lymphocyte receptor chain nucleic acid pairing. In one embodiment, the barcode-free approach is to, after partitioning a sample into subpopulations or sub-subpopulations (e.g., after the steps at FIG. 1, 1002 and/or FIG. 2, 2002 or 2005), randomly fuse the nucleic acid from individual containers together. The nucleic acid in one embodiment is amplified lymphocyte receptor chain amplified nucleic acid, e.g., from a PCR reaction, and/or expanded via cell expansion. The lymphocyte receptor chain nucleic acid fusion molecules are sequenced in a manner to maintain the fusion information; and bioinformatic analysis is used identify chains in partitioned subpopulations or sub-populations. A network of chain fusions is generated where each vertex of the network is a lymphocyte receptor chain, i.e., a TCR chain (alpha, beta, gamma, delta or variable domain thereof), a BCR chain (heavy or light chain or variable domain thereof) or an antibody chain (heavy or light). The network of chain fusions is then subjected to network analysis to identify (i) clusters of highly-interconnected chains, and (ii) which chains were present in the same starting container. Finally, statistical methods (e.g., assigning probability scores) are used to identify paired chains. Statistical methods are discussed further below.

Co-occurring receptor chains can be grouped together using the aforementioned network-analysis strategy, in one embodiment, based on the observations that (i) a sample subjected to the methods provided herein contains a substantial number of rare clones, such that after partitioning, a fraction of the cells occupying each container of a partitioned sample will only occur in one or a small number of partitions ii) the TCR/BCR/Ab chains arising from these rare cells can, together, be fused to nucleic acid arising from more frequent clone(s), thereby labeling the more frequent clone(s), thereby encoding co-localization information. Such a labelling strategy is fundamentally distinct from barcode approach in that the label isn't known a priori; sample demultiplexing only preserves co-occurrence information, not the precise starting container; accurate sample demultiplexing can only be accomplished retrospectively using the entirety of the data; and the label (e.g., the identity of a chain) can contain information which is useful for more than simply demultiplexing.

The network analysis-based demultiplexing approach is applicable over a range of starting parameters (e.g., number of partitions, number of lymphocytes or progeny cells per partition, fusions per chain) and accordingly is a robust alternative to the barcode approach.

The general barcode-free approach described in this example is to, after partitioning a sample comprising a plurality of lymphoctyes, (i) randomly fuse (i.e., operatively link or join) the nucleic acid encoding lymphocyte receptor chains in each partitioned sample, (ii) sequence these fusion molecules using a strategy that maintains the fusion information; (iii) perform bioinformatic analysis to identify chains, (iv) generate a network of fusions where each vertex is a T-cell receptor, B-cell receptor or antibody chain, or fragment thereof, and each edge is an observed fusion; (v) use network analysis to identify clusters of highly-connected chains, and (vi) assign clusters to starting container origin; and (vii) employ statistical methods to identify paired chains.

In one embodiment of this example, fusions are generated before cDNA synthesis (e.g., by fusing genomic DNA sequences or mRNA sequences) or during cDNA synthesis. Alternatively, if an amplification step is carried out, e.g., with PCR, fusions can be generated between first strand cDNA synthesis and amplification, during amplification or after amplification. In one embodiment, fusions are formed after an amplification step. Fusion of polypeptide chains can be carried out after cDNA synthesis and/or during an amplification step, for example, by the methods described in PCT Publication No. WO 2013/188872, incorporated by reference herein in its entirety for all purposes.

In one embodiment, lymphocyte receptor chain fusions are generated between chains of the same type, e.g., TCR α-α, TCR β-β, TCR γ-γ, TCR δ-δ, BCR/Ab heavy-heavy, BCR/Ab light-light). In another embodiment, lymphocyte receptor chain fusions are generated between chains of a different type, e.g., TCR α-β, TCR γ-δ, TCR γ-α, TCR γ-β, TCR δ-α, TCR δ-β, BCR/Ab heavy-light, TCR α-BCR/Ab heavy).

Using fusions to demultiplex samples eliminates the increased demands on oligonucleotide purity; reduces sample-handing stringency during library preparation (e.g., samples from the same vessel/container are expected to be much more connected than background contamination); eliminates experimental complexity as a result of large numbers of barcodes, thereby enabling the analysis of larger numbers of containers (e.g., thousands vs hundreds.

Importantly, the invention is not limited to the type of sequencer or sequencing methodology employed. Types of sequencers and sequencing technologies amenable for use with the methods presented herein include, but are not limited to, the Genome Sequencer 20/FLX (commercialized by 454/Roche); MiSEQ instrument (Illumina), 'Solexa 1G' (later named 'Genome Analyzer' and commercialized by Illumina/Solexa), SOLiD™ system (commercialized by Applied Biosystems), and Polonator G.007 (commercialized by Dover Systems). Other protocols amenable for use with the methods provided herein include Polony sequencing, Helioscope™ single molecule sequencing, Lynx Therapeutics' Massively Parallel Signature Sequencing (MPSS), 454 pyrosequencing, Ion Torrent™ (Life Technologies), DNA nanoball sequencing (via rolling circle amplification), and VisiGen Biotechnologies approach.

In one embodiment, an Illumina MiSEQ instrument is used. High throughput sequencing protocols are well known to those of ordinary skill in the art. See, e.g., Gupta (2008). Trends in Biotechnology 26, pp. 602-611; Metzker. (2010). Nature Reviews Genetics 11, pp. 31-46; Schuster (2008). Nature Methods 5, pp. 16-18; Shendure and Ji (2008). Nat. Biotechnol. 26, pp. 1135-1145, each of which is incorporated by reference in its entirety for all purposes.

After antibody and/or TCR sequencing, bioinformatics analysis is performed to determine all of the antibody and/or TCR sequences that are present in the sample, and to record which index each TCR and/or antibody sequence corresponds to, and therefore, which container the particular antibody or TCR sequence originated from.

Once sequencing is complete, either with a barcode approach, or a barcode-free approach, the distribution of each of lymphocyte receptor chain across subpopulations or sub-subpopulations is determined (FIG. 1, 1005; FIG. 2, 2008). Statistical probabilities are then calculated and assigned to chain pairs as a measure of whether the observed distribution of a chain pair is independent from the distribution of a second chain pair (FIG. 1, 1005; FIG. 2, 2008).

The statistical probabilities, in one embodiment, are the statistical probabilities that the observed chain pair occurrences is greater than what would be expected by chance. In a further embodiment, the statistical probabilities that the observed chain pair occurrences is greater than what would be expected by chance given that the chains of the observed chain pairs do not originate from the same clonal population of lymphocytes (or progenitors thereof).

Statistical probabilities can be calculated according to methods known to those of ordinary skill in the art. In one embodiment, statistical probabilities are calculated using a Fisher's exact test. One or more lymphocyte receptor chain pairs (e.g., one or more functional lymphocyte receptor chain pairs) is identified based on the calculated statistical probabilities (FIG. 1, 1006; FIG. 2, 2009). For example, one or more functional lymphocyte receptor chain pairs is identified based on the calculated statistical probability being lower than a predetermined likelihood cutoff.

In some embodiments, the calculated statistical probabilities comprises a calculated p-value for pairing of each lymphocyte receptor chain pair of unique first and second lymphocyte chains. In one embodiment, the calculated statistical probabilities comprises a probability that the unique first and second lymphocyte receptor chains jointly occupy as many or more containers than they are observed to jointly occupy, assuming no true pairing and given the number of containers occupied by the unique first lymphocyte receptor chain sequence and the number of containers occupied by the second lymphocyte receptor chain sequence.

To test not only whether lymphocyte receptor chains occur together in the same container, but also whether they occur at similar frequencies, a Pearson correlation can be applied. Alternatively, a modified Spearman rank correlation may be applied to overcome the Pearson correlation's sensitivity to outliers.

Figure 6:
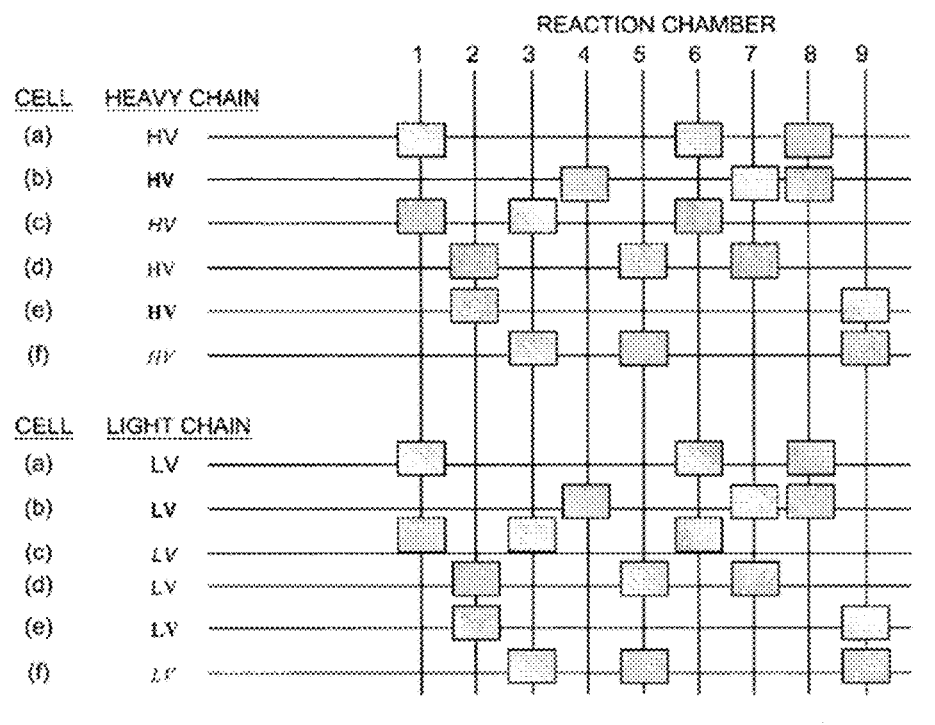
FIG. 6 is a matrix of heavy and light chains present in each reaction chamber, determined by sequencing the heavy and light chains, including an index sequence that was attached to each prior to, during, or after amplification.

For each possible lymphocyte receptor chain pair, the user determines if the two lymphocyte receptor chains are co-localized in a reaction more often than they would be localized by random chance (as determined by Binomial or Poisson statistics). It is recognized that in embodiments employing nucleic acid amplification (e.g., PCR), amplification may not be perfectly efficient and thus chains may not always appear together. Nevertheless, the user calculates a P-value for the co-localization and thus determines the probability of chain-pairing. This is used to generate a matrix of all heavy and light chain pairings with the value of the matrix determined by the P-value (see, e.g., FIG. 6).

EXAMPLES

The present invention is further illustrated by reference to the following Examples. However, it should be noted that these Examples, like the embodiments described above, are illustrative and are not to be construed as restricting the scope of the invention in any way.

Figure 11:
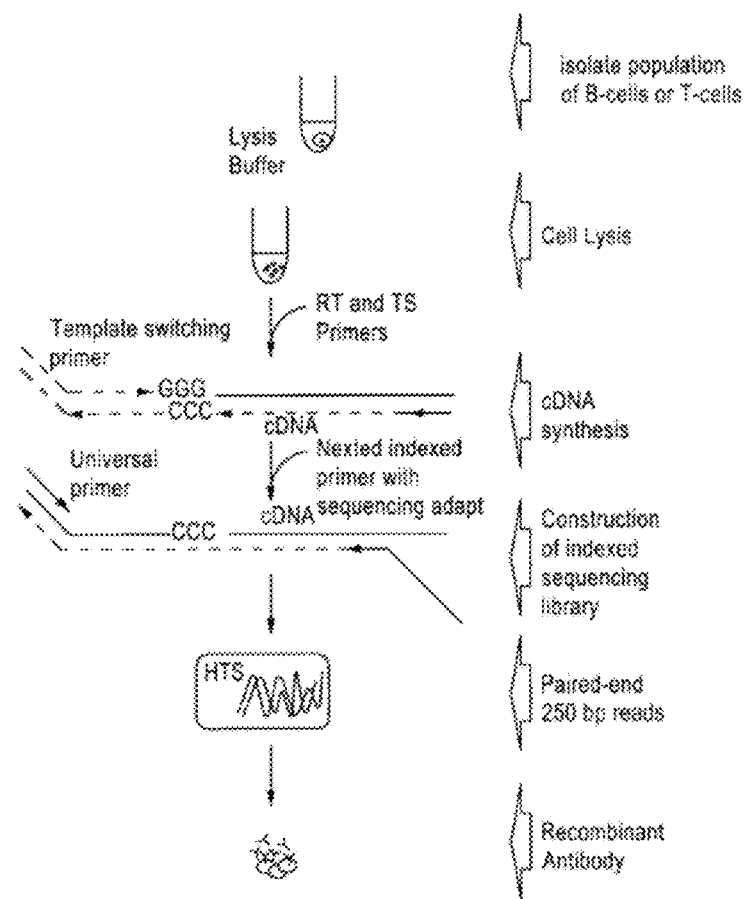
FIG. 11 is a schematic of an approach for identification of heavy chain variable regions (HV) and light chain variable regions (LV) using template-switching. Cells are deposited into individual microfuge tubes (for clarity, only one tube is depicted in the Figure), and cDNA is generated from multiplexed gene-specific primers targeting the constant region of heavy and light chains. Template-switching activity of MMLV enzyme is used to append the reverse complement of a template-switching oligo onto the 3' end of the resulting cDNA. Semi-nested PCR, using multiplexed primers that anneal to the constant region of heavy and light chain and a universal primer complementary to the copied template switching oligo, is used to amplify cDNA and introduce barcode sequences that are specific to each microfuge tube (container or vessel). Amplicons are then pooled and sequenced.
Figure 12:
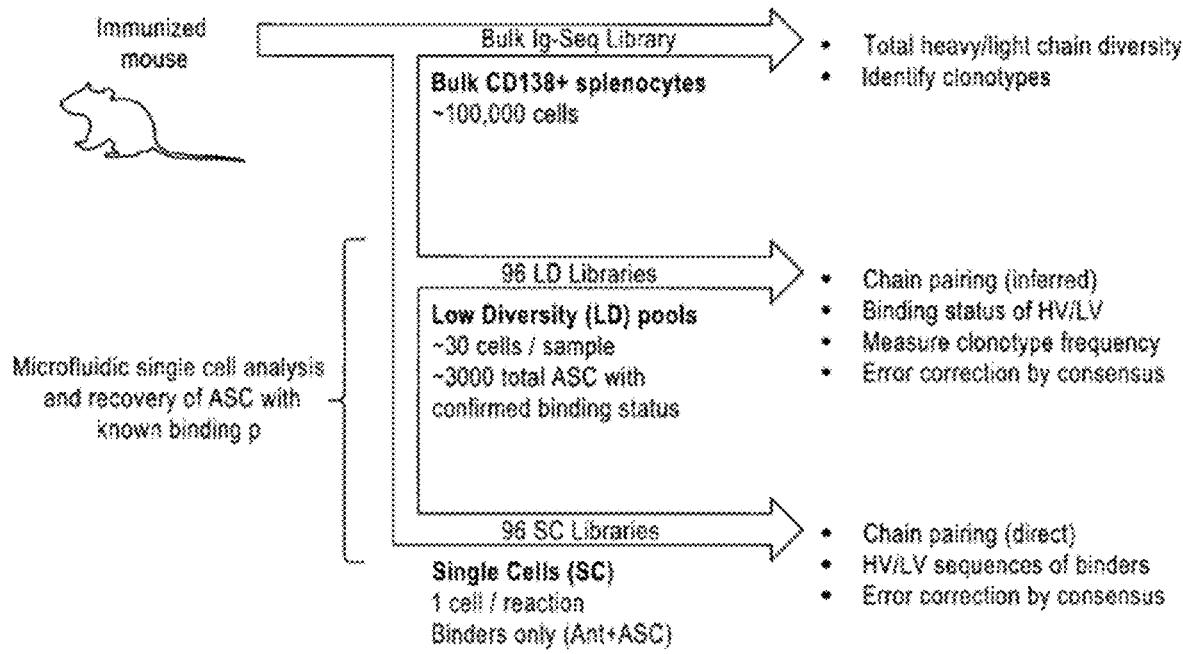
FIG. 12 is a schematic showing work flow to couple microfluidic single cell antibody analysis with Ig-Seq. Following immunization, ASCs are collected from the animal; a fraction of the ASCs are analyzed on microfluidic devices while the remaining are used for construction of a bulk amplicon library for high-throughput sequencing of the immunoglobin repertoire (Ig-Seq). From the microfluidic device, a total of 96 indexed single cell (SC) libraries and 96 indexed low diversity (LD) libraries are pooled for sequencing on MiSeq (Illumina). Analysis of the bulk library is used to determine HV and LV clonotypes present in the immune response, shown as clusters in FIG. 13.

Example 1—NGS Sequencing of Heterogeneous Populations of Antibodies or T Cell Receptors Antibody sequences were retrieved by combining template-switching and next-generation sequencing. Referring to FIG. 11, cells are deposited into microfuge tubes (one shown in the figure for simplicity) and cDNA is generated from multiplexed gene-specific primers targeting the constant region of heavy and light chains. Template-switching activity of MMLV enzyme is used to append the reverse complement of a template-switching oligo onto the 3' end of the resulting cDNA. Semi-nested PCR, using multiplexed primers that anneal to the constant region of heavy and light chain and a universal primer complementary to the copied template switching oligonucleotide, is used to amplify cDNA and introduce a unique barcode (indexing) sequences that is specific to each the amplicons in each particular container. Amplicons are then pooled and sequenced.

Example 2—Determination of Heavy Chain and Light Chain Pairing of Immunoglobulin Genes In principle, next-generation sequencing of immuno-globin genes (Ig-Seq) or T cell receptor genes can capture a comprehensive list of HV and LV sequences present within the antibody repertoire. However, the interpretation of these data sets is currently not possible. In this example, high-throughput antibody analysis platform is coupled with next-generation sequencing (e.g., Ig-Seq) to enable the functional interpretation of antibody repertoires from Ig-Seq analysis including assignment of binding specificity to sequences identified in Ig-Seq data, correct pairing of VH and VL chains across all major clonotypes, and accurate measurements of clonotype abundance.

Figure 14:
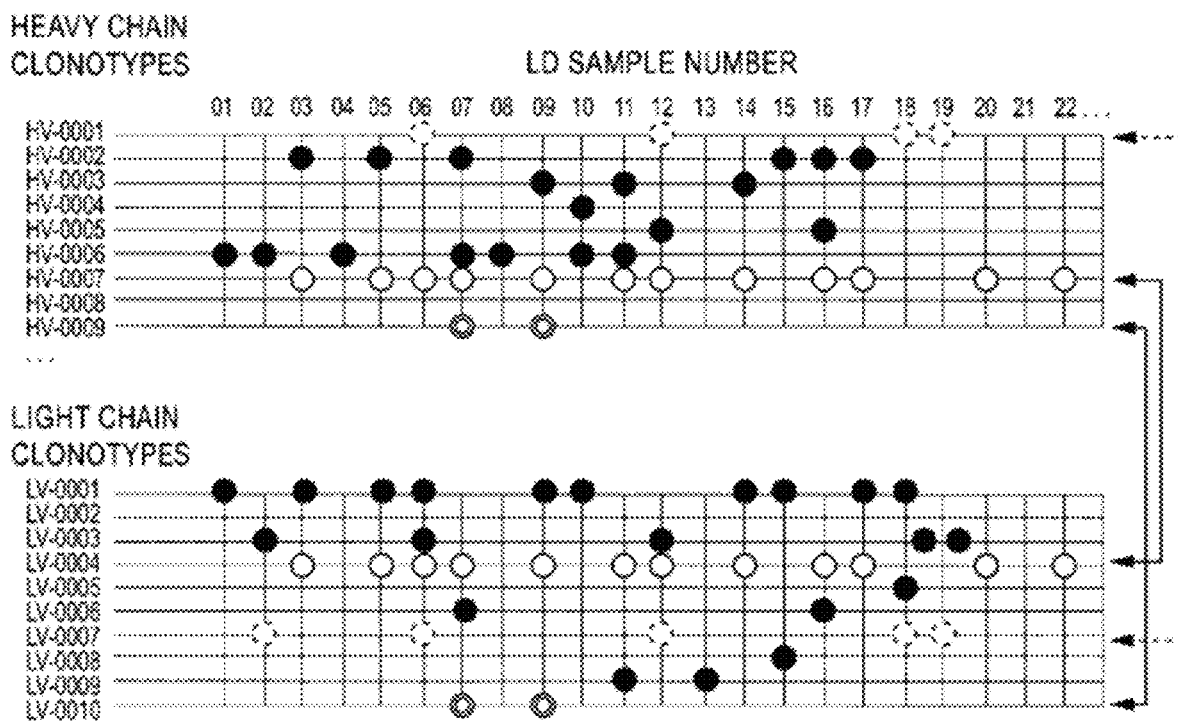
FIG. 14. Information on binding status and chain pairing for specific sequences allows interpretation of the bulk sample by assignment of binding status and clonotype pairing.
Figure 15:
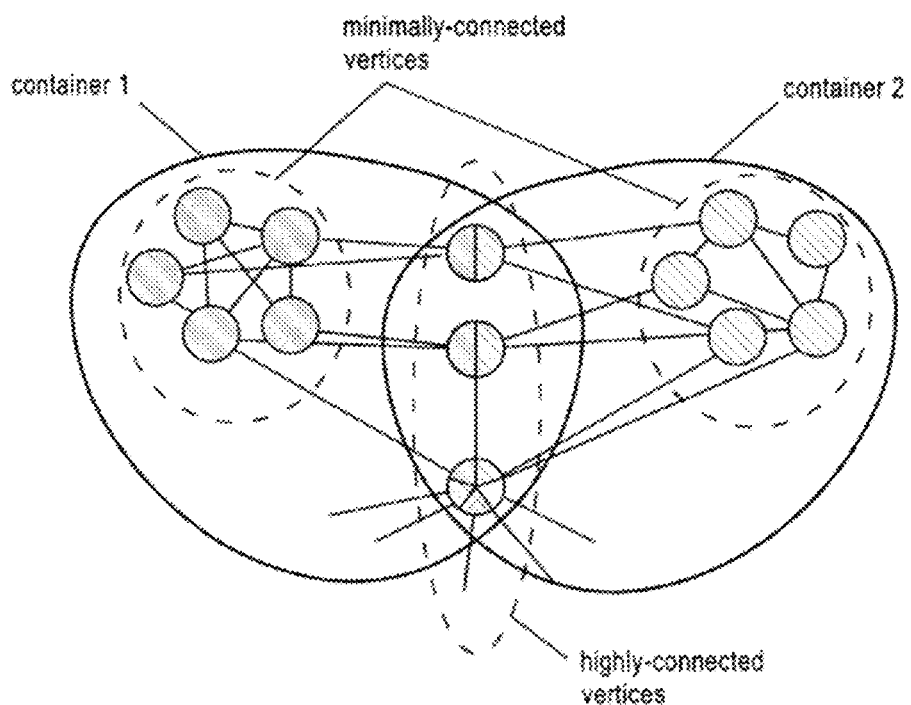
FIG. 15 is a diagram illustrating minimally-connected vertices, highly-connected vertices. Minimally connected verticies are first identified and later used to identify which starting containers the highly-connected verticies belong to. In this example there are two vertices which are found in both containers 1 and 2, and one vertex which is found in these two, plus an additional 3 different containers.
Figure 16:
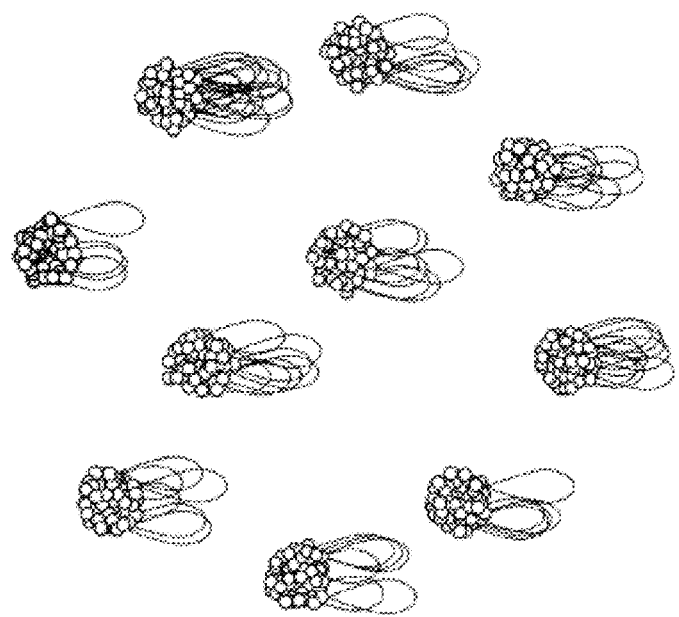
FIG. 16 Network diagram of the minimally-connected vertices identified from a partitioning and fusion simulation experiment with 100 cells partitioned into each of 10 wells and a read-depth of 10× per cell. Colours indicate the 10 different communities correctly identified using Walktrap community detection. These minimally-connected communities were used to correctly classify the highly-connected vertices.
Figure 17:
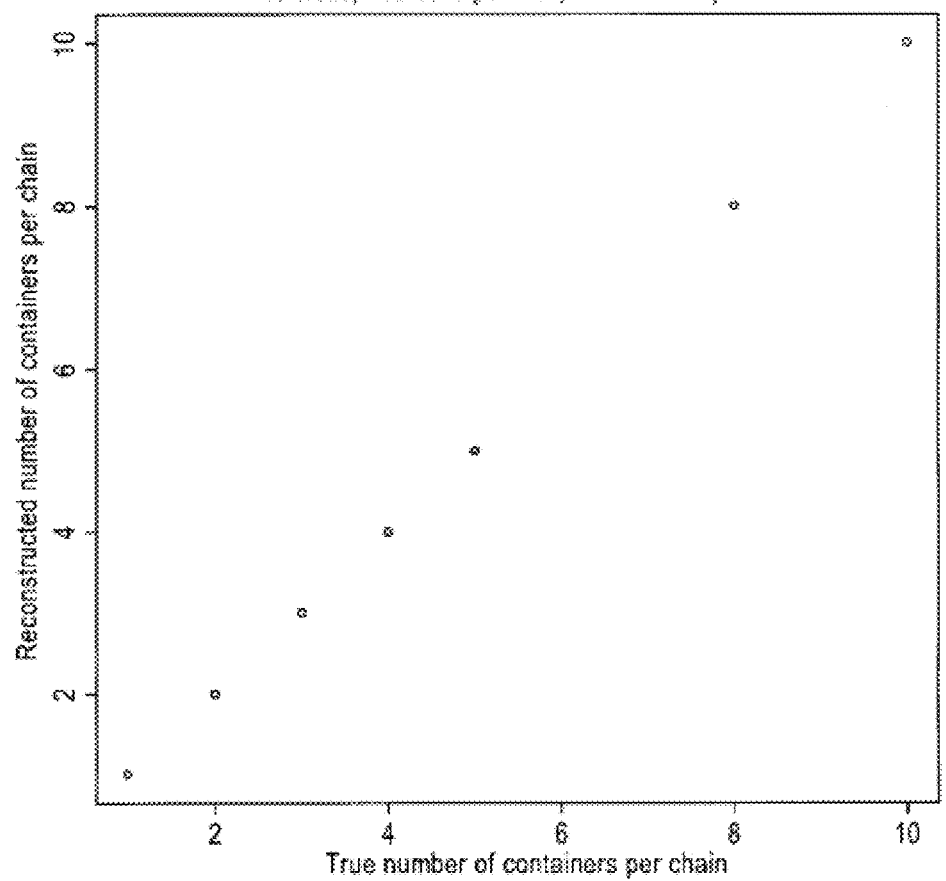
FIG. 17 is a scatter plot illustrating the number of reconstructed starting containers per chain versus the true number of starting containers for the same data presented in FIG. 16.

The workflow for the next generation sequencing strategy is shown in FIG. 14. ASCs are isolated from an immunized animal and a portion of these (~3000 ASCs) screened microfluidically, as described in PCT Publication No. WO 2014/153651, which published Oct. 2, 2014, which is incorporated by reference in its entirety for all purposes, to identify and assess the binding status and/or functional characteristics of the antibodies.

The remaining cells from the immunized animal are processed for bulk Ig-Seq as described below.

ASCs identified via microfluidic screening as having a particular functional effect, or binding characteristic, are then recovered and amplified to create 96 single cell (SC) libraries, capturing the most abundant clonotypes. All remaining ASCs are recovered and split into 96 equal sized pools, each having only antigen positive or antigen negative cells, to create low diversity (LD) libraries. Sequences obtained from all SC and LD samples are combined and used to interpret bulk Ig-Seq data.

Figure 13:
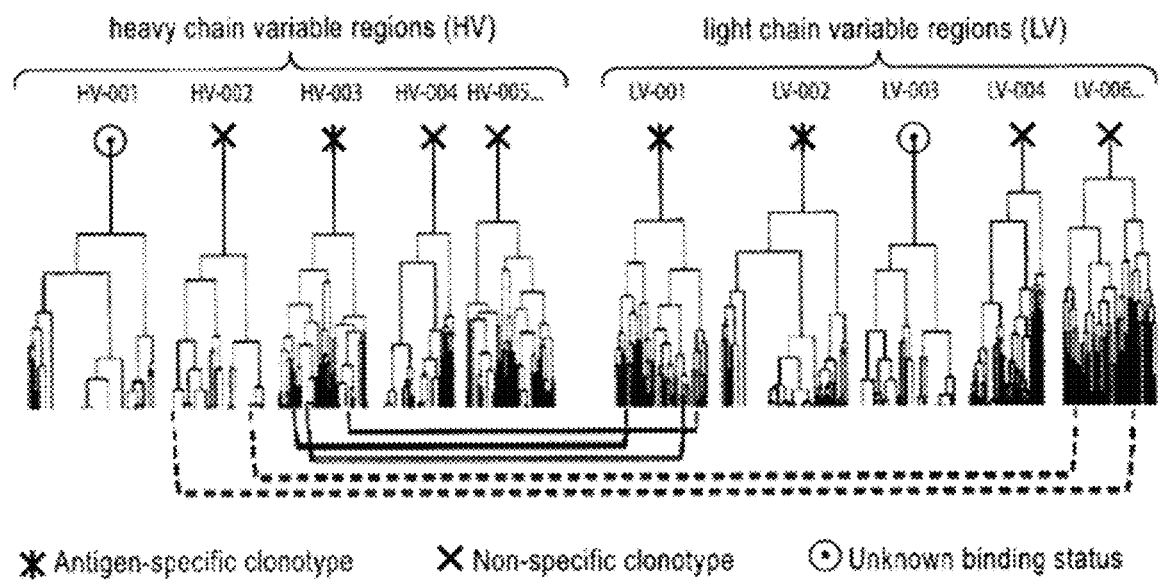
FIG. 13. Single cell libraries provide paired chain HV and LV sequences of mAbs from most abundant clonotypes that are confirmed to be antigen specific. Low diversity (LD) libraries provide additional identification of HV and LV sequences that are antigen specific or that are not antigen specific. LD libraries are also used to infer chain pairing by analysis of co-occurrence of HV and LV sequences across LD libraries, illustrated in FIG. 14.

Indexed Ig-Seq libraries for bulk, SC, and LD samples are made using a variant 5' rapid amplification of cDNA ends (RACE) that uses gene-specific template-switching reverse transcription (RT), followed by semi-nested PCR and next-generation amplicon sequencing (FIG. 13). Custom-designed multiplexed RT primers, targeting the constant regions of all heavy and light chain genes, are used to initiate a template-switching RT reaction. This approach is based on the ability of MMLV reverse transcriptase to append C nucleotides to the 3' end of a newly formed cDNA, followed by the extension of the cDNA using a "template switching primer" that binds to this overhang (Huber, et al. (1989). Journal of Biological Chemistry, 264(8): pp. 4669-4678; Luo and Taylor (1990). Journal of Virology 64(9), pp. 4321-4328, each of which is incorporated herein by reference in its entirety for all purposes). The resulting cDNA, with a 5' end determined by the constant region and a known sequence appended to the 3' end, is then amplified using a semi-nested approach (common 3' primers and multiplexed nested primers positioned inside the RT primer region). Primers used for this reaction include tails to append indexed sequencing adapters, thereby identifying the products from each sample. The resulting amplicon libraries are sequenced using paired end 250 base pair reads to generate merged reads that span the variable and leader sequence regions. Bulk Ig-Seq is performed on a dedicated flow cell.

Bulk, SC, and LD Ig-Seq data is combined and analyzed to identify HV and LV sequences and assigned these to clonotypes (FIG. 13). Merged paired-end reads are aligned against germline immunoglobin genes using Ig-BLAST (Ye et al. (2013). Nucleic Acids Research 41(W1): pp. W34-W40, incorporated by reference in its entirety) to determine chain usage and junctional structure. Heavy and light chains are then grouped into clonotypes based on common gene usage and CDR length. Hierarchical clustering within each clonotype is then be used to determine clonal structure and sequence variants. Finally, read frequency for each unique sequence is used to estimate relative abundance within the clonotype, as well as to establish a threshold for removal sequencing errors.

Antigen binding status (or functional property) is assigned to all sequences from clonotypes that include SC and LD derived sequences (shown as red and blue in FIG. 13). Next, SC samples with successfully identified heavy and light chain pairs are used to assign correct clonotype chain pairing, capturing the most abundant clonotypes (FIG. 13). Additional chain pairings will then be inferred from the LD samples by correlating the occurrence of identified HV and LV clonotypes across the 96 LD libraries (FIG. 14). Finally, the frequency of each of the clonotypes within the LD samples is used to determine the absolute clonotype frequency, on a cell-by-cell basis, according to a best estimate binomial statistic.

The approach outlined above is validated using PDGFRα/β as a model antigen. Following immunization of mice with the soluble extracellular domain of PDGFRα and PDGFRβ, binding to each target is screened for, and antigen-positive ASC(s) are recovered for Ig-Seq as described above. Inferred chain pairings from the LD samples are confirmed against those determined in the SC samples. Multiple inferred HV and LV pairs that are present at low frequency are synthesized and expressed to confirm binding specificity.

Finally, novel HV and LV sequences chosen from paired clonotypes of known binding specificity are synthesized. These HV and LV sequences are synthesized, cloned and expressed to test the hypothesis that Ig-Seq can be used to infer additional related sequences that are functional and may have improved properties.

Example 3—CXCR4 Antibody Profiling

The method outlined above is used to examine epitope coverage obtained by antibodies produced in different hosts against CXCR4 and with different immunization approaches. Rabbit and mouse antibody repertoires are analyzed and used to express antibodies from multiple clonotypes that span a range of relative abundance. For each of these epitope recognition using commercially available arrays for shotgun mutagenesis mapping (Integral Molecular) is determined. This directly tests the idea that rabbit antibodies, which are generated by gene conversion, have greater diversity and broader epitope coverage.

Ig-Seq analysis is used to evaluate how antigen-specific diversity and clonal structure changes in response to multiple immunizations. These data are informative regarding the optimal number of boosts prior to antibody selections if diversity is paramount, rather than the level of response or average affinity. Finally, different immunization strategies are evaluated to see what effect these may have on antibody diversity. This includes the use of pre-activated dendritic cells, which are known to enhance responses against weak antigens, and rapamycin, which has been recently shown to increase the diversity of epitopes recognized during vaccinations (Keating et al. (2013). Nature Immunology 14(12) p. 1266. Next, mAbs that block CXCR4 signalling are screened for using the methods outlined in PCT Publication No. WO 2014/153651, which published Oct. 2, 2014, which is incorporated by reference in its entirety for all purposes. From these mAb, Ig-Seq analysis is used to identify and synthesize 10 additional HV and 10 additional LV sequences. These sequences are then cloned to make 100 pairwise combinations of new antibodies, which are expressed and tested for blocking activity. In addition to establishing a new "rational" approach to antibody optimization, these experiments provide insight into whether affinity maturation selects heavy and light chains independently or in a coupled fashion.

Example 4—Barcode Free Library Construction and Chain Pair Identification

This example provides a barcode free approach (fusion approach) to generating nucleic acid fusion molecules to identify lymphocyte receptor chain pairs.

Drawbacks to barcode-based sample identification include (i) significantly increased demands on oligonucleotide purity due to the well-documented barcode contamination during oligonucleotide synthesis and purification; (ii) increased demands on sample handling due to the high chance of index cross-contamination during liquid handling; (iii) dramatically increased experiment complexity as the number of samples increases (e.g., the number of barcodes required to uniquely label N samples scales linearly for commonly used single-indexing, or sqrt(N) for dual-indexing approaches; (iv) misidentification of read origin due to sequencing and/or synthesis errors in the barcode sequence; and (v) the inability to identify read origin due to sequencing and/or synthesis errors. A barcode-free approach is thus desirable.

The network analysis-based demultiplexing approach can be applied over a range of starting parameters (e.g., number of partitions, number of lymphocytes or progeny cells per partition, fusions per chain). To show this, a simulation of random partitioning of clones replicating a measured bulk clonotype distribution, and the random fusion of the chains within each container was carried out. An example algorithm for determining the initial starting chain partition patterns was then implemented. Under the conditions used in this example, the original colocalization for all the tested parameters was correctly determined. Results of the simulation are provided in FIGS. 15-18.

An example demultiplexing algorithm is:
Construct a network such that each vertex is a unique chain and each edge is an observed fusion;
Identify vertices that are found in only one partition (the minimally-connected vertices) using, for example, node degree. Vertices having a lower degree are more likely to be found in only one partition.
Temporarily remove the vertices not meeting this criteria (i.e., the highly-connected vertices) from the graph.
Employ community detection algorithms on the resulting reduced network. For example, the Walktrap community detection algorithm can be used herein, as described in *Pascal Pons, Matthieu Latapy: Computing communities in large networks using random walks*, arXiv:physics/0512106 [physics.soc-ph], incorporated by reference herein in its entirety. Each vertex is then assigned to a community.
For each of the highly-connected vertices:
  a. The adjacent minimally-connected vertices is found;
  b. A consensus list of communities that each adjacent minimally-connected vertex belongs to is generated; and
  c. The highly-connected vertex is assigned to all of these communities.

Example 5—Combined Analysis of T and B Cell Receptor Pairs

Gene-specific 5' rapid amplification of cDNA ends (RACE) is performed on cDNA encoding lymphocyte receptor chain pairs, followed by one round of multiplexed PCR, which specifically amplifies the genes of interest while adding the necessary barcode sequences and sequencing adapters and priming sites. The implementation differs from other reports in that the design of both the oligonucleotides and amplification conditions allows the final sequencing construct to be assembled in only one round of PCR, as opposed to e.g. the two rounds reported in WO2014/145992. The construct design allows a minimum number of specific primers to be used, ultimately improving amplification efficiency by reducing the need for earful optimization of reaction conditions and primer sets, errors due to mispriming of degenerate primer sets and, formation of primer-dimers and non-specific amplification products.

cDNA is first generated using a gene-specific primer from the gene of interest. Upon reaching the end of the transcript, the terminal-transferase activity of MMLV-derived reverse transcription enzymes adds non-templated nucleotides to the end of the cDNA. These non-templated bases then allow the hybridization of a supplied oligonucleotide (the "template-switching" oligonucleotide), which allows the RT enzyme to "template-switch" and copy the template-switching oligo. This is commonly referred to as "template-switching" or "SMART/SMARTer (Switching Mechanism at 5' End of RNA Template) cDNA synthesis." A unique molecular identifier (UMI) can, optionally, be included as part of the template-switching oligo to assist in correcting quantitation biases and sequencing/polymerase errors.

There are three types of oligonucleotides included in the multiplexed PCR: a forward universal (EU), a reverse universal (RU), and a set of forward gene-specific primers (FG). The forward and reverse universal primers each contain: a platform-specific sequencing adapter, an index sequence and a universal sequence. Each of the gene-specific primers contains a gene-specific region (usually within the constant region) and the complement of a portion of the universal sequence used in the reverse universal primer.

FU and RU are included at the PCR-brew at standard concentrations. Each FU, however, is included at limiting concentrations to reduce the side-products and inhibitory effects that primers these can produce. Under these conditions, exponential amplification is only achieved when the reverse universal primer extends using one of forward gene-specific primers as a template. This extended universal primer can then anneal to the template strand in subsequent cycles.

Example 6—Experimental Workflow with Microfluidics

In one method, a population of lymphocytes, or progeny thereof, e.g., a B cell or T cell population is isolated from an animal. The population of cells is activated and caused to divide several times (e.g., from about 2 to about 10 times, also described herein as "expanded" cell population). The resulting population is partitioned into a plurality of different containers, for example 100 different containers (i.e., to create 100 different subpopulations). Optionally, after splitting the population of cells into a plurality of subpopulations, the subpopulations are activated and caused to undergo further divisions (e.g., from about 1 to about 10 divisions). The cell subpopulations are used to create, for example, 100 barcoded sequencing libraries of lymphocyte receptor chains. The co-occurrence of lymphocyte receptor chain pairs is used to infer chain pairing. In a further embodiment, prior to creating the barcoded sequencing libraries, the population of lymphocytes or progeny thereof is first analyzed in a microfluidic assay to determine one or more properties of one or more lymphocyte receptors present in the population.

In yet another embodiment, population of lymphocytes, or progeny thereof is isolated from an animal. The population is caused to divide at least once (e.g., from about 1 to about 10 times). The resulting population is partitioned into subpopulations and each subpopulation is subjected to microfluidic analysis to determine one or more properties of one or more lymphocyte receptors present in the population. Functional subpopulations are recovered and lymphocyte receptor chains are sequenced, either with a barcode approach or a barcode free approach, as described herein. Optionally, prior to sequencing, the functional subpopulations are partitioned into sub-subpopulation. In the case of a barcode approach, the partitioned subpopulations or sub-subpopulations are used to create a barcoded sequencing library of lymphocyte receptors, wherein each barcode corresponds to a unique container from which the lymphocyte receptor nucleic acid was derived. The co-occurrence lymphocyte receptor chains is used to infer chain pairing.

Example 7—TCR Chain Pairing Analysis

Sequencing reads are split by well partition (container) barcodes. Next, reads originating from the same container are split into alpha and beta reads based on the constant-region primer sequence. MiTCR (Bolotin DA., et al. *MiTCR: software for T-cell receptor sequencing data analysis. Nat. methods* 10.9, 813-814 (2013)) is then run on each set of reads (e.g., 192 sets for a 96 well plate), for partial correction of sequencing and PCR errors, and extraction of the CDR3 and variable, joining, constant, and diversity regions. The presence of each alpha chain across the containers is then summarized in table format, with the rows as chain names, columns as container numbers, and each entry of the table being the number of reads observed for that chain in the respective container. The same is carried out for beta chains. See Table A below as an example for one specific alpha chain and one specific beta chain.

TABLE A

Container reads for an alpha chain and a beta receptor chain.

| | 1 | 2 | 3 | 4 | 5 | 6 | 7 | 8 | 9 | 10 | 11 | 12 | 13 | 14 | 15 | 16 | 17 | 18 | 19 | 20 | 21 |
|---|---|---|---|---|---|---|---|---|---|---|---|---|---|---|---|---|---|---|---|---|---|
| α-0001 | ● | | | | ● | ● | | | | | | | | | | | | ● | | ● | ● |
| β-0001 | ● | | | | ● | | | | | | | | | ● | | | | ● | | ● | ● |

Contingency Table

| | | α-0001 | |
|---|---|---|---|
| | | Present | Absent |
| β-0001 | Present | 5 | 1 |
| | Absent | 1 | 89 |

The occurrence pattern of each alpha chain is then compared with the occurrence pattern of each beta chain (i.e., each alpha row is compared with beta row, see Table A), with significant co-occurrence indicating a putative pair. Significance can be determined using a number of different statistical tests, as known to those of ordinary skill in the art.

If the occurrence patterns are converted to binary, present/absent readouts (e.g. a chain is present if it occurs at ≥x reads, or absent if occurs at <x reads), a contingency table can be constructed for each potential alpha-beta pairing (see above). Fisher's exact test can is then performed, generating a p-value for the potential pairing.

With the noise present in real data, however, the determination of "presence" and "absence" is not a trivial exercise. Sources of noise include: barcode contamination, PCR inefficiencies, PCR errors, and cell-to-cell variability in the number of TCR transcripts expressed. Establishing presence or absence using the same read cut-off for all chains is not sufficient, as the noise differs between chains (i.e., the noise for a high frequency clone may be on the same level as the signal for a low-frequency clone). Even if it is possible to accurately model the noise and determine true presence and absence, the loss of information inherent to converting to binary can result in pairings that are biologically irrelevant. For example, a significant "pair" determined by the Fisher's exact test might be a low frequency (e.g. 0.05%) alpha chain with a high frequency (2%) beta chain. It is unlikely that the number of alpha transcripts and the number of beta transcripts in a certain cell would differ this dramatically.

To test not only whether alpha and beta chains occur together in the same wells, but also whether they occur at similar frequencies, a Pearson correlation can be applied. Alternatively, a modified Spearman rank correlation may be applied to overcome the Pearson correlation's sensitivity to outliers.

While the above example refers to pairing of T cell receptor chains, it is equally applicable to antibody heavy/light chain pairing, with MiGEC (Shugay M et al. *Towards error-free profiling of immune repertoires. Nature Methods* 11, 653-655 (2014)) taking the place of MiTCR.

All, documents, patents, patent applications, publications, product descriptions, and protocols which are cited throughout this application are incorporated herein by reference in their entireties for all purposes.

The embodiments illustrated and discussed in this specification are intended only to teach those skilled in the art the best way known to the inventors to make and use the invention. Modifications and variation of the above-described embodiments of the invention are possible without departing from the invention, as appreciated by those skilled in the art in light of the above teachings. It is therefore understood that, within the scope of the claims and their equivalents, the invention may be practiced otherwise than as specifically described.

---

The invention claimed is:

1. A method for identifying a functional immunoglobulin (Ig) heavy and Ig light chain pair in a sample comprising antibody secreting cells (ASCs), comprising:

partitioning the sample into a plurality of individual vessels to provide a plurality of sample subpopulations;

performing a functional assay on one or more of the sample subpopulations, wherein the functional assay measures a property of an Ig heavy and Ig light chain pair;

identifying one or more functional subpopulations based on the results of the functional assay;

lysing the ASCs in the one or more functional subpopulations;

amplifying the Ig heavy and Ig light chain nucleic acid;

attaching a unique DNA barcode to the Ig heavy and Ig light chain nucleic acid in each functional subpopulation, wherein the unique DNA barcode sequence identifies the functional subpopulation from which the Ig heavy and Ig light chain nucleic acid originated;

pooling the barcoded Ig heavy and Ig light chain nucleic acid; sequencing the barcoded Ig heavy and Ig light chain nucleic acid to determine the identity of the Ig heavy and Ig light chains in each functional subpopulation;

determining the observed distribution of each of the Ig heavy and Ig light chains across the functional subpopulations and calculating statistical probabilities that the observed distributions of Ig heavy and light chain pairs in the sample subpopulations are independent from one another; and identifying the functional Ig heavy and light chain pair based on the calculated statistical probabilities.

2. The method of claim 1, further comprising, prior to the partitioning the sample step, subjecting the sample to conditions suitable for expansion of one or more of the ASCs.

3. The method of claim 1, further comprising, prior to the lysing step, subjecting one or more of the functional subpopulations to conditions suitable for expansion of one or more of the ASCs in the one or more of the functional subpopulations.

4. The method of claim 1, further comprising partitioning one or more of the functional subpopulations into a second plurality of individual vessels prior to the lysing step to form one or more partitioned functional subpopulations.

5. The method of claim 4, further comprising, prior to the lysing step, subjecting one or more of the partitioned functional subpopulations to conditions suitable for expansion of one or more of the ASCs in the one or more partitioned functional subpopulations.

6. The method of claim 1, wherein the nucleic acid is cDNA derived from mRNA expressed by the antibody secreting cells (ASCs) in each subpopulation.

7. The method of claim 1, wherein the nucleic acid is mRNA and further comprising, performing a first strand cDNA synthesis reaction on the mRNA prior to the amplifying step.

8. The method of claim 7, wherein the first strand cDNA synthesis reaction is specific for Ig heavy and Ig light chain mRNA.

9. The method of claim 8, wherein at the first strand cDNA synthesis comprises first strand cDNA synthesis of the variable regions of the Ig heavy and Ig light chain mRNA.

10. The method of claim 1, wherein identifying the plurality of Ig heavy and Ig light chain pairs comprises identifying one or more Ig heavy and Ig light chain pairs that are expressed by an antibody secreting cell (ASC) present at a frequency of about 1 cell to about 50 cells in the sample, at a frequency of about 1 cell to about 40 cells in the sample, at a frequency of about 1 cell to about 30 cells in the sample, at a frequency of about 1 cell to about 20 cells in the sample, at a frequency of about 1 cell to about 10 cells in the sample, or at a frequency of about 1 cell to about 5 cells in the sample.

11. The method of claim 2, wherein subjecting the sample to conditions suitable for expansion comprises cell culture of the plurality of antibody secreting cells (ASCs) and polyclonal activation.

12. The method of claim 2, wherein subjecting the sample to conditions suitable for expansion comprises cell culture of the plurality of antibody secreting cells (ASCs) and antigen-specific activation.

13. The method of claim 2, wherein subjecting the sample to conditions suitable for expansion comprises treating the sample with Epstein Barr virus, CD40L, or one or more toll like receptor agonists.

14. The method of claim 13, wherein the Toll-like receptor agonist is LPS, CpG, R848, or PWM.

15. The method of claim 11, wherein polyclonal activation results in about 1 to about 10 divisions, on average, of the plurality of antibody secreting cells (ASCs).

16. The method of claim 12, wherein antigen-specific activation results in about 2 to about 10 divisions on average, or about 3 to about 10 divisions on average, of the antibody secreting cells (ASCs).

17. The method of claim 1, wherein the plurality of individual vessels comprises from about 25 to about 1,000 individual vessels, from about 25 to about 900 individual vessels, from about 25 to about 800 individual vessels, from about 25 to about 700 individual vessels, from about 25 to about 600 individual vessels, from about 25 to about 500 individual vessels, from about 25 to about 400 individual vessels, from about 25 to about 300 individual vessels, from about 25 to about 200 individual vessels, or from about 25 to about 100 individual vessels.

18. The method of claim 1, wherein calculating the statistical probabilities comprises calculating the statistical probabilities that the observed chain pair occurrences are greater than what would be expected by chance given that the chains of the observed chain pairs do not originate from the same clonal population of antibody secreting cells (ASCs).

19. The method of claim 1, wherein sequencing the nucleic acid clonotypes comprises sequencing fusion pairs of Ig heavy and Ig light chain pairs.

20. The method of claim 19, wherein the fusion pairs comprise BCR/Ab heavy-heavy, BCR/Ab light-light, BCR/Ab heavy-light, or a combination thereof.

21. The method of claim 19, wherein the fusion pairs are sequenced in a manner to maintain the fusion information.

22. The method of claim 19, further comprising generating a network of lymphocyte receptor chain fusion pairs and subjecting the network to network analysis to identify (i) clusters of highly-interconnected chains, and (ii) which chains were present in the same individual container.

23. The method of claim 1, wherein the functional assay is an antibody binding assay.

24. The method of claim 23, wherein the assay is an ELISA assay.

25. The method of claim 1, wherein the functional assay is an antibody affinity or specificity assay.

26. The method of claim 1, wherein the functional assay is an antibody ELISPOT assay.

27. The method of claim 1, wherein the functional assay is a cytokine neutralization assay, a virus neutralization assay or an enzyme neutralization assay.

28. The method of claim 1, wherein the functional assay is a signaling assay to determine whether one or more antibodies expressed by the ASCs has agonist or antagonist activity.

29. The method of claim 1, wherein the functional assay is an antibody-dependent cell mediated cytotoxicity (ADCC) assay.

30. The method of claim 1, wherein the functional assay is a complement dependent cytotoxicity assay (CDC) assay.

31. The method of claim 1, wherein the functional assay is a cell growth modulation assay.

32. The method of claim 1, wherein the functional assay is an autophagy assay.

* * * * *